US008148132B2

(12) United States Patent
Mehtali et al.

(10) Patent No.: US 8,148,132 B2
(45) Date of Patent: Apr. 3, 2012

(54) PRODUCTION OF VIRAL VACCINES IN SUSPENSION ON AVIAN EMBRYONIC DERIVED STEM CELL LINES

(75) Inventors: Majid Mehtali, Coueron (FR); Patrick Champion-Arnaud, Nantes (FR); Arnaud Leon, Nantes (FR)

(73) Assignee: Vivalis, Roussay (FR)

( * ) Notice: Subject to any disclaimer, the term of this patent is extended or adjusted under 35 U.S.C. 154(b) by 298 days.

(21) Appl. No.: 11/918,206

(22) PCT Filed: Apr. 11, 2006

(86) PCT No.: PCT/EP2006/061531
§ 371 (c)(1),
(2), (4) Date: Oct. 11, 2007

(87) PCT Pub. No.: WO2006/108846
PCT Pub. Date: Oct. 19, 2006

(65) Prior Publication Data
US 2009/0081251 A1      Mar. 26, 2009

Related U.S. Application Data

(60) Provisional application No. 60/728,807, filed on Oct. 21, 2005.

(30) Foreign Application Priority Data

Apr. 11, 2005 (FR) .................................. 05 03583

(51) Int. Cl.
*C12N 1/00* (2006.01)
*C12N 5/0375* (2006.01)
(52) U.S. Cl. ........................................ 435/237; 435/363
(58) Field of Classification Search .................. None
See application file for complete search history.

(56) References Cited

U.S. PATENT DOCUMENTS 7,432,101 B2 * 10/2008 Guehenneux et al. ...... 435/235.1
2004/0058441 A1    3/2004 Pain et al.

FOREIGN PATENT DOCUMENTS

| EP | 1 260 581 | 11/2002 |
| EP | 1 500 699 | 1/2005 |
| WO | WO 97/37000 | 10/1997 |
| WO | WO 03/077601 | 9/2003 |
| WO | WO 2005/007840 | 1/2005 |
| WO | WO2005/007840 A1 * | 1/2005 |

OTHER PUBLICATIONS

Sigmal-Aldraich G6148 on line catalog 2009.*
Invitrogen on line catalog for McCyo medium 2009.*
Biomedical Family on line Catalog on 2009.*
Gibco BRL catalog published in 2000-2001, p. (1-48).*
Acloque et al., "Indentification of a New Gene Family Specifically Expressed in Chicken Embyronic Stem Cells and Early Embryo", Mechanisms of Development, vol. 103, pp. 79-91, 2001.
Enami et al., "High-Efficiency Formation of Influenza Virus Transfectants", Journal of Virology, vol. 65, No. 5, pp. 2711-2713, May 1991.
Eyal-Giladi et al., "From Cleavage to Primitive Streak Formation: A Complementary Normal Table and a New Look at the First Stages of the Development of the Chick", Developmental Biology, vol. 49, pp. 321-337, 1976.
Kempe et al., "Smallpox Vaccination of Eczema Patients with a Strain of Attenuated Live Vaccinia (CVI-78)", Pediatrics, vol. 42, No. 6, pp. 980-985, Dec. 1968.
Meltzer et al., "The Economic Impact of Pandemic Influenza in the United States: Priorities for Intervention", Emerging Infectious Diseases, vol. 5, No. 5, pp. 659-671, Sep.-Oct. 1999.
Merten, "Development of Serum-Free Media for Cell Growth and Production of Viruses/Viral Vaccines—Safety Issues of Animal Products Used in Serum-Free Media", Dev. Biol., vol. 111, pp. 233-257, 2002.
Pain et al., "Long-Term In Vitro Culture and Characterization of Avian Embryonic Stem Cells with Multiple Morphogenetic Potentialities", Development, vol. 122, pp. 2339-2348, 1996.
Pain et al., "Chicken Embryonic Stem Cells and Transgenic Strategies", Cells Tissues Organs, vol. 165, pp. 212-219, 1999.
Simonsen et al., "The Impact of Influenza Epidemics on Mortality: Introducing a Severity Index", American Journal of Public Health, vol. 87, No. 12, pp. 1944-1950, Dec. 1997.
Sugimoto et al., "Characteristics of an Attenuated Vaccinia Virus Strain, LC16m0, and Its Recombinant Virus Vaccines", Vaccine, vol. 12, pp. 675-681, 1994.
Tartaglia et al., "HYVAC: A Highly Attenuated Strain of Vaccinia Virus", Virology, vol. 188, pp. 217-232, 1992.

* cited by examiner

*Primary Examiner* — Bao Li
(74) *Attorney, Agent, or Firm* — Buchanan Ingersoll & Rooney PC

(57) ABSTRACT

The present invention relates to the development and manufacturing of viral vaccines, particularly the industrial production of viral vectors and vaccines, and more particularly the use of avian embryonic stem cells, preferably the EBx cell line derived from chicken embryonic stem cells, for the production of viral vectors and viruses; the invention is particularly useful for the industrial production of viral vaccines to prevent viral infection of humans and animals.

26 Claims, 14 Drawing Sheets

Figure 1:
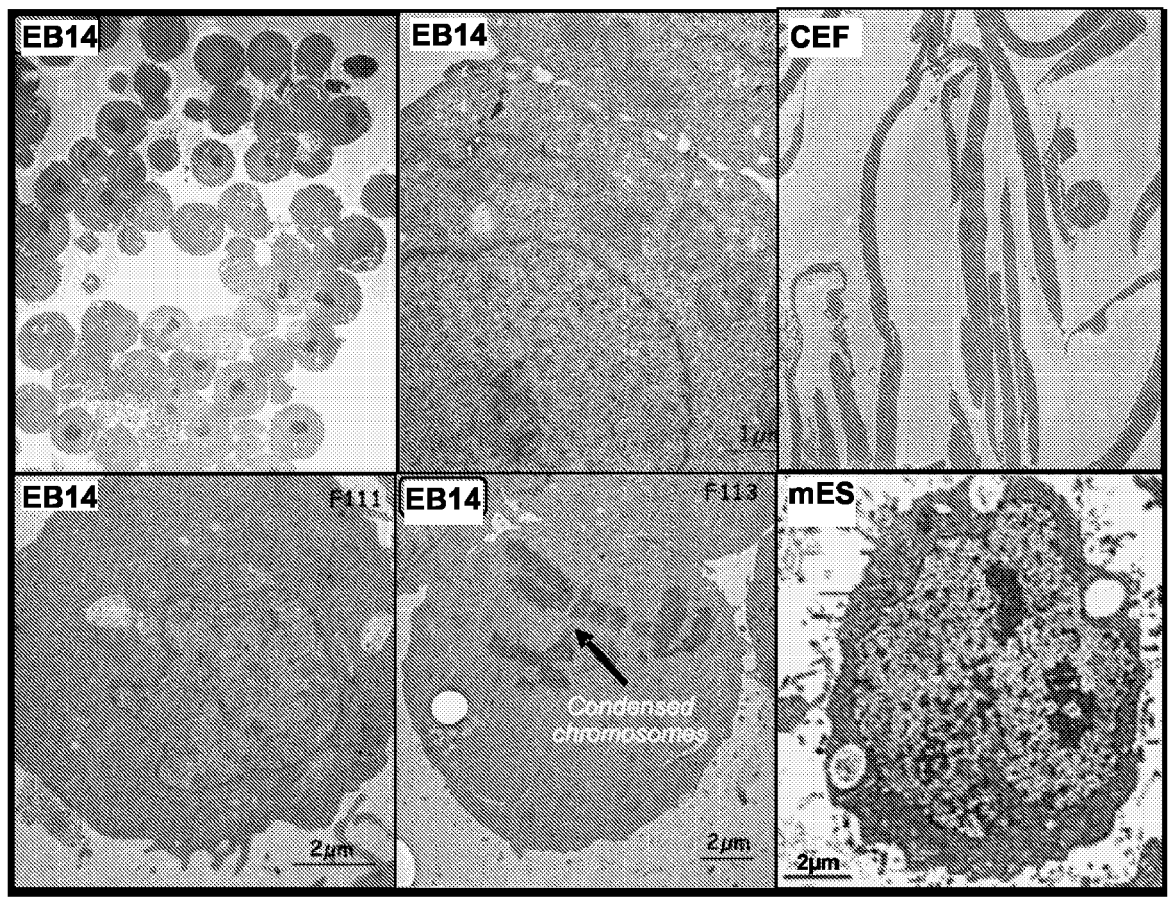

PAGE 10% Precast Biorad, 75mM β-mercaptoethanol ; 4µL supernatant

PRODUCTION OF VIRAL VACCINES IN SUSPENSION ON AVIAN EMBRYONIC DERIVED STEM CELL LINES

CROSS-REFERENCE TO PRIORITY/PCT/PROVISIONAL APPLICATIONS

This application claims priority under 35 U.S.C. §119 of FR 05/03583, filed Apr. 11, 2005, and of Provisional Application No. 60/728,807, filed Oct. 21, 2005, and is a continuation of PCT/EP 2006/061531 filed Apr. 11, 2006 and designating the United States, published in the English language as WO 2006/108846 A1 on Oct. 19, 2006, each hereby expressly incorporated by reference in its entirety and each assigned to the assignee hereof.

The present invention relates to the development and manufacturing of viral vaccines. In particular, the invention relates to the field of industrial production of viral vectors and vaccines, more in particular to the use of avian cells, preferably chicken embryonic derived stem cell line, for the production of viral vectors and viruses. The invention is particularly useful for the industrial production of viral vaccines to prevent viral infection of humans and animals.

BACKGROUND

Mass vaccination would be the simplest and most effective approach to control viral pandemics, such as pandemic and inter-pandemic flu outbreaks, but also to prevent bioterrorist threat, such as the recent terrorist acts involving anthrax in the USA. However, for many viral vaccines such as influenza and smallpox vaccines that are currently produced on egg-based systems, it is most likely that the current production capacity of vaccines manufacturers would not suffice to cover the needs in a case of a pandemics or a bioterrorist attack.

At unpredictable intervals, and in addition to seasonal mild influenza epidemics caused by antigenic drift or reassortment, antigenic shifts with completely new influenza virus subtypes emerge against which immunity in the human population does not exist. They cause global pandemics that spread rapidly around the world. Three of these pandemics occurred in the last century (1918, 1957, 1968). The most severe in 1918, infected approximately 50% of the world's population, of about 25% suffered clinical disease; the total mortality was estimated between 20-40 million, particularly affecting people in the prime of their lives. This pandemic depressed population growth for the following ten years. The last outbreak with high mortality and pandemic potential occurred in 1997, when a new influenza virus (H5N1) emerged in Hong Kong, killing a third of the affected patients, mainly young adults. Fortunately, the virus was not able to spread from person to person and it was possible to quickly stop the outbreak. A similar virus was isolated in 2003 in Hong Kong. In the USA, the impact of the next pandemic is projected to be 18-42 million outpatient visits, 314,000-734,000 hospitalizations and 89,000-207,000 deaths, assuming that the next pandemic will be of a similar magnitude as the 1957 or the 1968 pandemic, and not like the 1918 pandemic (Meltzer M I, Cox N J and Fukuda K. *The economic impact of pandemic influenza in the United States: priorities for intervention. Emerging Infectious Diseases* 1999; 5:659-671). Extrapolating this projected impact proportionally to the global population, the gross estimate of the global impact of the next pandemic can be estimated at 1-2 billion cases of the flu, 5.3-12.3 million cases of severe illness and 1.5-3.5 million deaths.

Beside a potential pandemic, annual influenza epidemics caused by drifted variants of influenza A and B viruses infect about 10-20% of the population each season, and cause febrile illness, hospitalizations and deaths. Indirect statistical methods have been used to estimate the total burden of influenza; these include various statistical models that quantify the seasonal increase in morbidity and mortality during influenza epidemic periods (Simonsen L, Clarke M J, Williamson G D, Stroup D F, Arden N H, Schonberger L B. *The impact of influenza epidemics on mortality: introducing a severity index. Am J. Public Health* 1997; 87:19441950). Using this methodology, an average influenza season in the USA is currently associated 25-50 million cases of flu, 150,000 hospitalizations, and 20,000-40,000 deaths. Assuming that the age-specific risk of influenza morbidity is similar to that in the USA, the annual average global burden of inter-pandemic influenza may be on the order of around 1 billion cases of flu, around 3-5 million cases of severe illness and 250,000-500,000 deaths (see *WHO report Geneva, April* 2003: *State of the art of new vaccines Research & Development—Initiative for Vaccine Research*).

The currently available influenza vaccines are effective in preventing inter-pandemic influenza-related illness and highly effective in terms of preventing hospitalizations and deaths. In spite of these results, in developed and in developing countries, none of the "high risk population" have been reached as of yet, due in part to the relatively high price of the vaccine and the need for annual re-vaccination. However, very recently, the use of the influenza vaccine has begun to increase worldwide to reach around 235 millions doses in 2003, but there is still a sizeable gap in pandemic vaccine demand as the current vaccine production. Indeed the World Health Organization (WHO) estimates that there are about 1.2 billion people at "high risk" for severe influenza outcomes (elderly over 65 years of age, infant, children, adults with chronic health problems, health care workers, . . . ).

The current egg-based system used to produce licensed influenza vaccines, despite being reliable for more than 50 years, shows its limitations that include:

a lengthy, cumbersome and resource-consuming manufacturing process that requires the procurement and quality control of large quantities of eggs for each individual production campaign. This current egg-based production system does not incite additional pharmaceutical companies to go into the business of egg-derived flu vaccines because the potential profit margin is too thin;

the need to select which virus strains will be in the vaccine at least 6 months in advance of the influenza season. This early decision about which strains to include in the influenza vaccine will not always be correct, and the long lead time required to produce the vaccine makes midstream corrective action impossible;

the need to produce enough influenza vaccine each year to meet continually increasing demand (about 250 millions doses in industrialized countries in 2004, about 100 millions doses for the USA only). The recent shortfall of influenza vaccines in the USA during winter 2004-2005 due to a contamination in the UK-based plant of an egg-derived flu vaccines manufacturer highlight this issue. Moreover, the current global production capacity of influenza vaccine does not even suffice to cover parts of the global "high risk" population. In reality, it is questionable whether the global infrastructure would be able to handle timely distribution and delivery of pandemic influenza vaccine;

the requirements of hundreds of millions of fertilized chicken eggs to manufacture the vaccine with the associated risks of insufficient supply of eggs in cases of epidemic infections in donor chicken flocks;

the need in cases of life attenuated influenza virus to use costly specific pathogen free (SPF) chicken eggs;

the inflationist costs associated with the use of bovine sera originating from BSE-exempt countries;

the allergenicity of egg-derived components in some individuals;

the inability to use eggs for the propagation of viruses that are highly virulent and lethal to chickens.

In addition, current vaccine technology produces vaccines with a narrow spectrum of production, and it is therefore most unlikely that vaccines available in stockpiles would protect against a completely new influenza virus pandemic strain.

Alternatively, the bioterrorist threat became a major concern for numerous western-countries governments in those past years such as the recent terrorist acts involving anthrax. The United States government takes appropriate measures for rapid diagnosis, defense and reaction to biological attacks through the implementation of the Bioterrorism Preparedness and Response Act in 2002. Biological weapons are indeed relatively accessible and constitute for the bioterrorist organizations a cheap and efficient way to threaten and frighten populations and governments. In particular, the use of the smallpox virus as a biological weapon have increased in recent years and several countries have developed contingency plans to deal with such a risk.

Smallpox is considered as having the greatest potential to cause widespread damage in case of deliberate dissemination, followed by plague, anthrax and botulism. Smallpox was declared eradicated in 1980, and all world countries have since then stopped their vaccination programs. This has led to a steady decline in population immunity to viral infection, which makes of the smallpox virus an even more dangerous agent in case of bioterrorist release. The US Center for Disease Control (CDC) has classified the smallpox as a class A bioterrorist agent, i.e. among the most dangerous micro-organisms given its easy propagation and high mortality rate.

Rapid mass vaccination would be the ideal approach to control an outbreak of smallpox. The US government has taken the lead by securing additional vaccine stock, vaccinating military personnel and key healthcare workers, and establishing a programme for the development of a safe vaccine that could be given to the entire population regardless of their health status. Other governments are monitoring the USA's progress as well as assessing their own emergency preparedness.

In the recent past, governments were either acquiring or producing their own first-generation stocks in state-owned laboratories or issuing commercial tenders. First generation vaccines that were harvested directly from animals, were shown to be effective; however, they were often containing impurities and bacteria that greatly increase the chance of adverse reactions and complications specially in immunocompromised individuals. Since the eradication of smallpox, a limited number of pharmaceutical companies were able to quickly step in and produce smallpox vaccines. Of that group still fewer are able to produce second-generation vaccines using Dryvax® and Lister-Elstree vaccinia strains in qualified cell cultures according to good manufacturing practice standards. However, as with the first-generation, these vaccines are also not suitable for immune-compromised individuals. A mass vaccination with first and second generation vaccines could lead to complications that would kill one in a million individuals and cause serious disease in 10 times more cases. Consequently, a safer third generation vaccine has been developed by even fewer pharmaceutical companies. Third generation vaccines are based on a strain of the Modified Vaccinia Ankara (MVA) virus used during the smallpox eradication campaign in Germany in the 1970's. In clinical trials, MVA was administered without significant side-effects to about 150,000 individuals, including many considered at risk for the conventional smallpox vaccination.

All these smallpox vaccines are produced on primary chicken embryo fibroblasts isolated from chicken embryos. These production systems are associated with several serious limitations, including:

a lengthy, cumbersome and resource-consuming manufacturing process that requires the procurement and quality control of large quantities of eggs or CEFs for each individual production campaign;

the need in many cases to use costly specific pathogen free (SPF) chicken embryos;

the risks of insufficient supply of eggs in cases of epidemic infections in donor chicken flocks;

the inflationist costs associated with the use of bovine sera originating from BSE-exempt countries;

the allergenicity of eggs in some-individuals;

the inability to use eggs for the propagation of viruses that are highly virulent and lethal to chickens.

While the egg-based and CEFs production process remain relatively reliable process, an efficient cell-based production system would represent a significant improvement in providing a faster, cheaper and less cumbersome method for growing viruses. Moreover, in the event of a flu pandemic, a cell culture based manufacturing process offers additional advantages:

the production of the influenza vaccine can start immediately after the pandemic strain has been identified, isolated and distributed;

there is no need to wait for the development of so-called High Growth Reassortants (viruses adapted to high yield growth in embryonated hens eggs) necessary for production in eggs;

the availability of the first vaccine batch would be approximately 9 weeks after the receipt of the strain, instead of 6-9 months with the egg-derived process;

a cell-derived process allows the production of strains that cannot be adequately grown in eggs (e.g. Avian Hong Kong Flu in 1997);

there is no problem of egg shortage during pandemics.

Moreover, the use of cell lines for manufacture of viral vaccines, instead of egg or CEF platforms, would have the additional following advantages in connection with the safety of the vaccine: no antibiotic additives present in the vaccine formulation; no toxic preservatives (such as thiomersal) needed; reduced endotoxin levels, no egg allergy issue; growth in protein and serum free media (no adventitious agent/BSE); high purity of virus vaccine preparation.

There is therefore an urgent need to improve on the current viral vaccine production technologies based on eggs or chicken-embryonic fibroblasts. The development of cell-culture platforms as an alternative to the eggs and CEF production systems for the manufacture of viral vaccines is likely the most rapid and promising solution to overcome current vaccine production bottlenecks and time constrains. Moreover, cell-culture production technologies would improve possibilities of up-scaling of vaccine production capacities in face of a pandemic or a terrorist attack.

Based on these specific requirements, the inventor has taken advantage of its expertise in avian biology and in avian embryonic stem (ES) cells to undertake the development of novel stable avian cell lines that enables the efficient replication of human and veterinarian vaccines and vaccine candidates, and that fulfil the industrial, regulatory and medical specifications. Using a proprietary process (see WO 03/076601 and WO 05/007840), the inventor has thus generated a series of well characterized and documented cell lines (the EBx® cells) that are derived from chicken ES cells with no steps of genetic, chemical or viral immortalization. EBx® cells have been generated using a fully documented 2 steps process, and taking in consideration regulatory requirements:

Step 1: Isolation, In Vitro Culture and Expansion of Chicken ES Cells:

Embryonic stem cells are unique in that (i) they can self-renew indefinitely in vitro as undifferentiated cells, (ii) they have unlimited regenerative capacity, (iii) they maintain a stable chromosomal content; (iv) they express high levels of telomerase and specific cell-surface markers. Despite many efforts worldwide, ES cells have been successfully isolated from only a very limited number of species (mouse, human, monkeys). The inventor has dedicated significant resources over the last years to isolate and establish ES cells from various avian species. Such research efforts led to the successful isolation and characterization of chicken ES cells [Pain et al. 1999. Cell Tissues Organs 165: 212-219]. The inventor then developed proprietary procedures that allow the efficient in vitro culture and large-scale expansion of chicken ES cells without induction of differentiation.

Step 2: Derivation of EBx® Cells:

Then the inventor established a proprietary process to derive stable adherent and suspension cell lines from chicken ES cells. The process includes the progressive withdrawal of serum, feeder cells and growth factors from the cell culture medium and the adaptation of cells to a suspension culture. These embryonic derived chicken cell lines maintained most of the desirable features of ES cells (i.e. indefinite proliferation, expression of ES specific markers such as the telomerase, stability of the karyotype) but in addition displayed new "industrial-friendly" characteristics (growth in suspension in serum-free media).

Figure 2:
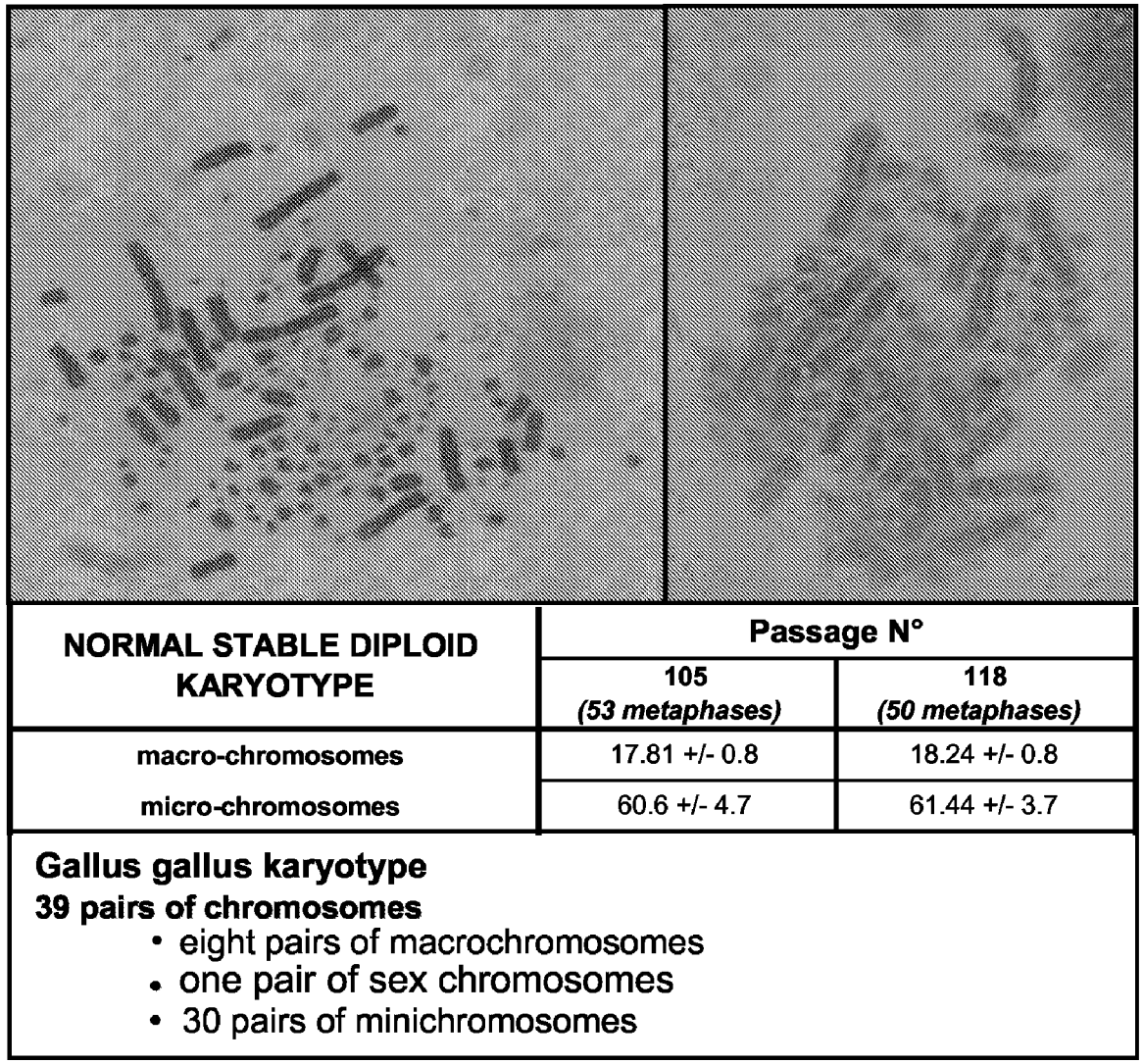
Figure 3:
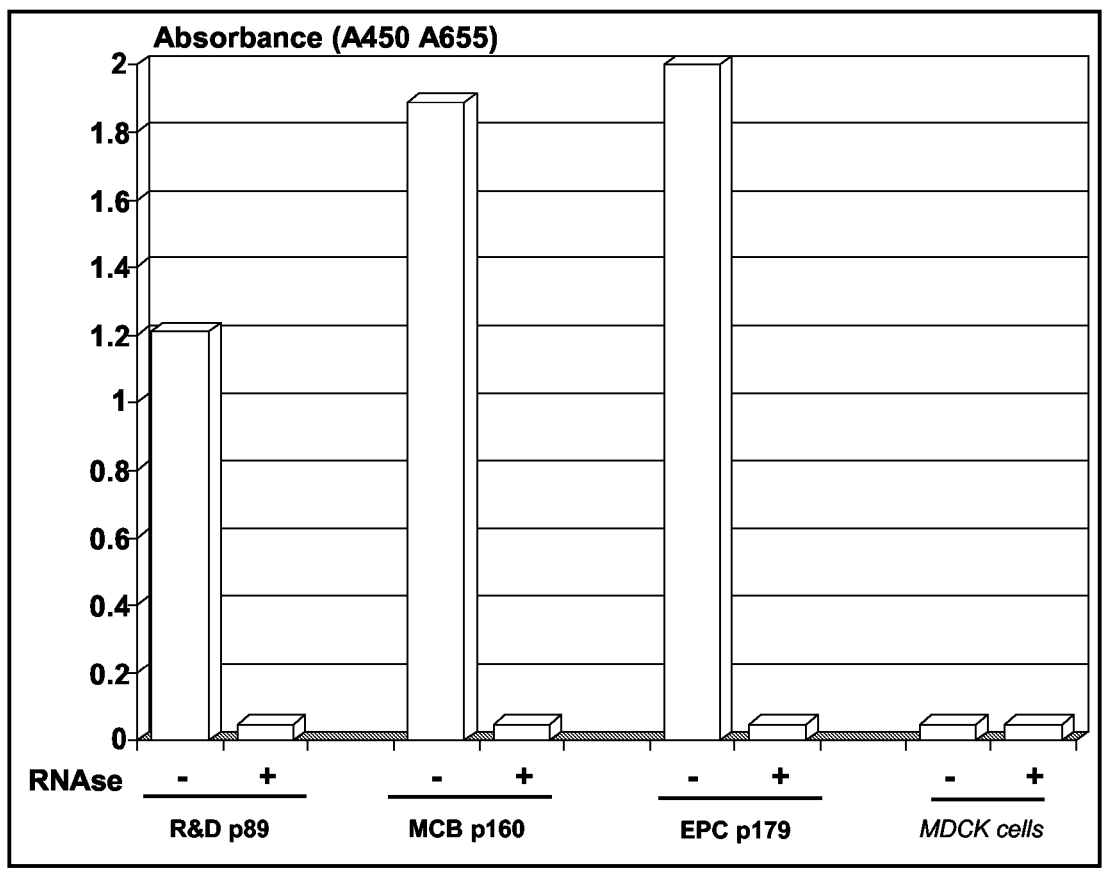
Figure 4:
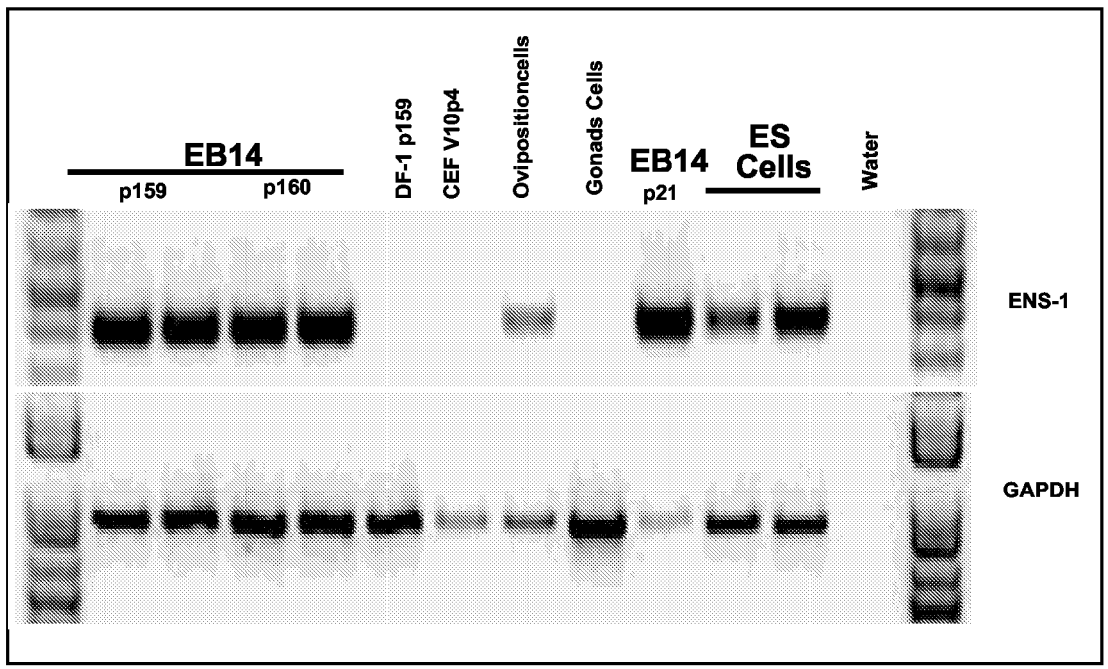

Based on their attractive biological properties, the inventor selected some chicken EBx® cell lines for further development, such as adherent cell lines EB45 (also named S86N45 in WO 03/076601 and WO 05/007840), from which suspension cell line EB14 has been derived. More preferably the chicken EBx® cells of the invention are selected among EB45 and EB14 cell lines. In a more preferred embodiment, the chicken EBx® cell line is EB14 or its sub-clone EB14-074. For the sake of simplicity, EB14 and EB14074 will be herein named EB14. EB45 and EB14 cells display an embryonic stem cells phenotype (i.e. high nucleo-cytoplasmic ratio) under long term culture (>150 passages). EB45 and EB14 cells are small cells with a large nucleus and nucleolus, and display short pseudopodia extending from the plasma membrane (FIG. 1). EB45 and EB14 cells are highly metabolically active, and present a ribosome and mitochondria rich cytoplasm. A genetic analysis of EB45 and EB14 cells showed that they are male, diploid and genetically stable over the generations (FIG. 2). EB45 and EB14 cells express alcaline phosphatase, stem cells-specific cell surface markers, such as EMEA-1 and SSEA-1 (FIG. 5) and the ES cells-specific ENS1 gene (FIG. 4). Of particular importance EB45 and EB14 cells also express high levels of telomerase enzymatic activity which is stably maintained throughout passages (FIG. 3). Telomerase is a key enzyme in that it promotes continuous cell growth and chromosomal stability. Three weeks and 2.5 months tumorigenicity analysis performed in the immuno-suppressed new-born rat model showed that EB14 cells are non-tumorigenic in vivo. EB45 and EB14 cells are characterized by a very short generation time around 16 hours at 39° C. (the body temperature of chicken) and around 20 h at 37° C. These cell lines present therefore unique properties that make them more efficient, safer and cost-effective cell substrates for the industrial production of viral vaccines such as influenza and smallpox vaccines.

The EBx® cells, and more specifically the EB14 cells of the invention would be of high value for the manufacturing of influenza and smallpox vaccines as well as other major human and animal viral vaccines (Table 1) currently produced on embryonated eggs or on chicken primary fibroblasts, such as the measles, mumps, yellow fever vaccines or investigational poxviruses against infectious diseases such HIV or cancers. Current data have already demonstrated the ability of EBx® cell line, and more specifically to replicate several recombinant and wild-type viruses. For example, preliminary experiments have established that EBx® cells support the replication of influenza virus (see the French priority document patent application FR 05 03583 filed on Apr. 11, 2005, Example 3, pages 30 to 41) and Modified Vaccinia virus Ankara (MVA) (see WO 05/007840).

TABLE 1

| AVIAN | SWINE | EQUINE | HUMAN | RECOMBINANT |
|---|---|---|---|---|
| influenza virus | influenza virus | influenza virus | Smallpox | Canarypox |
| reovirus | | Eastern equine encephalomyelitis | influenza virus | Fowlpox |
| fowlpox virus | | Western equine encephalomyelitis | measles virus | Modified Vaccinia Virus Ankara (MVA) |
| canarypox virus | | | Mumps virus | Alphavirus - Sinbis virus |
| chicken poxvirus | | | Rabies | Alphavirus - Samliki Forest Virus |
| psittacine herpes virus | | | Yellow level virus | Alphavirus - Venazuelan EEV |
| Newcastle Disease Virus | | | thick borne encephaslitis | Avian Adenovirus - CELO |
| falcon herpes virus | | | | |
| pigeon herpes virus | | | | |
| infectious bursal disease virus | | | | |
| infectious bronchitis virus | | | | |
| Marek's disease virus | | | | |
| turkey herpes virus | | | | |
| chicken anemia virus | | | | |
| avian encephalomyelotis virus | | | | |
| polymavirus type I & II | | | | |
| Adenovirus type I, II, & III | | | | |

The above listed unique properties of EBx® cells, and more specifically EB14 cells, imply the development of a specific process for manufacturing viral vaccines in EBx® cells. Indeed, without to be bound by a theory, the high metabolic level of EBx® cells request that the cell culture medium provide enough energy to cells in order to assure cell growth and viral replication. The aim of the present invention is to provide an innovative and efficient manufacturing process based on the avian embryonic derived stem cells EBx®, more specifically EB14 cells, for the industrial production of a viral vaccines that are currently produced in eggs and in CEFs.

DESCRIPTION

The instant invention provides a process of replicating a virus in avian embryonic derived stem cells EBx®, more preferably in EB14 cells, said process comprising the steps of
infecting an EBx cell culture with a virus of interest; said EBx cells being preferably cultured in animal serum free medium;
culture of infected EBx cells in order to replicate said virus; harvest the virus in cell culture supernatant and/or inside said cells.
According to a preferred embodiment, said process comprises the steps of
a) proliferating said EBx®, more preferably EB14 cells, in a cultivation vessel, in suspension, in a serum-free medium N° 1;
b) infecting said cells with the selected virus when the cell density is of at least 1.5 million cells/ml;
c) shortly before infection, simultaneously to infection, or shortly after infection adding to the cell culture serum-free medium N° 2; and
d) further culturing said infected cells in order to allow virus replication; and
e) optionally, harvesting said virus.

The term "virus" as used herein includes not only naturally occurring viruses but also attenuated viruses, reassortant viruses, vaccine strains, as well as recombinant viruses and viral vectors, and so on. The virus of the invention are preferably selected from the group consisting of adenoviruses, hepadnaviruses, herpes viruses, orthomyxoviruses, papovaviruses, paramyxoviruses, picornaviruses, poxviruses, reoviruses and retroviruses.

In a preferred embodiment, the viruses, the related viral vectors, viral particles and viral vaccines belong to the family of poxviruses, and more preferably to the chordopoxyiridae. In one embodiment, the virus or the related viral vectors, viral particles and viral vaccines is an avipoxvirus selected among fowlpox virus, canary pox virus (i.e. ALVAC), juncopox virus, mynahpox virus, pigeonpox virus, psittacinepox virus, quailpoxvirus, sparrowpoxvirus, starling poxvirus, turkey poxvirus. According to another preferred embodiment, the virus is a vaccinia virus selected among Lister-Elstree vaccinia virus strain, modified vaccinia virus such as Modified Vaccinia virus Ankara (MVA) which can be obtained from ATCC (ATCC Number VR-1508), NYVAC (Tartaglia et al., 1992 Virology 188: 217-232), LC16m8 (Sugimoto et Yamanouch 1994 Vaccine 12:675-681), CV178 (Kempe et al., 1968 Pediatrics 42: 980-985) and other recombinant or non-recombinant vaccinia virus.

In another preferred embodiment, the viruses, the related viral vectors, the viral particles and vaccines belong to the family of orthomyxoviruses, in particular influenza virus. The influenza virus is selected from the group consisting of human influenza virus, avian influenza virus, equine influenza virus, swine influenza virus, feline influenza virus. Influenza virus is preferably selected in strains A, B and C. Among strains A, one can recite viruses with different subtypes of haemagglutinin and neuraminidase, such as without limitation H1N1, H2N2, H3N2, H4N2, H4N6, H5N1, H5N2, H7N7 et H9N2. Among H1N1 strains, one can recite A/Porto Rico/8/34, A/New Caledonia/20/99, A/Beijing/262/95, A/Johannesburg/282/96, A/Texas/36/91, A/Singapore. Among strains H3N2, one can recite A/Panama/2007/99, A/Moscow/10/99, A/Johannesburg/33/94. Among B strains, one can recite without limitation B/Porto Rico/8134, B/Johannesburg/5/99, B/Vienna/1/99, B/Ann Arbor/1/86, B/Memphis/1/93, B/Harbin/7/94, N/Shandong/7/97, B/Hong Kong/330/01, B/Yamanashi/66/98. The influenza Virus of the invention is selected among wild type virus, primary viral isolate obtained from infected individual, recombinant virus, attenuated virus, temperature sensitive virus, low-temperature adapted virus, reassortant virus, reverse genetic engineered virus.

When the virus of the invention is influenza virus, the process of the invention comprises the additional step of adding proteolytic enzyme in the culture medium in conditions that allow virus propagation. The proteolytic enzyme is selected from the group consisting of trypsin, chymotrypsine, thermolysine, pepsine, pancreatine, papaïne, pronase, subtilisine A, elastase, furine and carboxypeptidase. According to a preferred embodiment, the enzyme is trypsin. The final concentration of trypsin in cell culture medium is comprises between around 0.5 to 1 mg/ml up to 25 mg/ml. More preferably, the final concentration of trypsin in cell culture medium is comprised between 0.01 to 10 usp/ml (usp: US pharmacopea unit) preferably around between 0.05 to 2 usp/ml, more preferably around between 0.3 to 1 usp/ml. Preferably, the proteolytic enzyme is a recombinant protein produced on a procaryotic host.

In another preferred embodiment, the viruses, the related viral vectors, the viral particles and vaccines belong to the family of paramyxoviruses, in particular measles virus, Newcastle Disease virus, mumps virus and rubella viruses.

In another preferred embodiment, the viruses, the related viral vectors, the viral particles and vaccines belong to the family of bimavirus, in particular Infectious Bursal Disease virus.

Recombinant viruses include but are not limited to viral vectors comprising a heterologous gene. In some embodiments, a helper function(s) for replication of the viruses is provided by the host cell EBx®, a helper virus, or a helper plasmid. Representative vectors include but are not limited to those that will infect avian or mammalian cells.

The term <<avian>> as used herein is intended to refer to any species, subspecies or race of organism of the taxonomic class <<ava>>, such as, but not limited to, such organisms as chicken, turkey, duck, goose, quails, pheasants, parrots, finches, hawks, crows, ostrich, emu and cassowary. The term includes the various strains of *Gallus gallus*, or chickens (for example White Leghorn, Brown Leghorn, Barred-Rock, Sussex, New Hampshire, Rhode Island, Australorp, Minorca, Amrox, California Gray, Italian Partidge-colored), as well as strains of turkeys, pheasants, quails, duck, ostriches and other poultry commonly bred. In a preferred embodiment, the avian cell of the present invention is a chicken cell.

The cultivation vessel of the invention is more preferably selected among continuous stirred tank bioreactor, Wave™ Bioreactor, Bello™ bioreactor, spinner flask, flask and a cell factory. Typically, cells are scaled-up from a master or working cell bank vial through various sizes of T-flasks or roller bottles and, preferably, finally to bioreactors. The resulting cell suspension is then typically fed into a seed production bioreactor (typically 20-30 L volume) for further cultivation, and in some embodiments, to a larger production bioreactor (typically 150-180 L volume). The ratio of volume of the second (larger) bioreactor to the seed bioreactor depends upon the degree to which the cell line is propagated in the first bioreactor, but is typically from 3:1 to 10:1, e.g., in the range of (6-8):1. According to a preferred embodiment, the cultivation vessel is a continuous stirred tank bioreactor that allows control of temperature, aeration, pH and other controlled conditions and which is equipped with:

appropriate inlets for introducing the cells, sterile oxygen, various media for cultivation, etc.;

outlets for removing cells and media; and means for agitating the culture medium in the bioreactor.

According to the present invention, "serum-free medium" (SFM) meant a cell culture medium ready to use, that is to say that it does not required serum addition allowing cells survival and cell growth. This medium is not necessary chemically defined, and may contained hydrolyzates of various origin, from plant for instance. Preferably, said SFM are "non animal origin" qualified, that is to say that it does not contain components of animal or human origin (FAO status: "free of animal origin"). In SFM, the native serum proteins are replaced by recombinant proteins. Alternatively SFM medium according to the invention does not contain protein (PF medium: "protein free medium") and/or are chemically defined (CDM medium: "chemically defined medium"). SFM media present several advantages: (i) the first of all being the regulatory compliance of such media (indeed there is no risk of contamination by adventitious agents such as BSE, viruses); (ii) the optimization of the purification process; (iii) the better reproducibility in the process because of the better defined medium. Example of commercially available SFM media are: VP SFM (InVitrogen Ref 11681420, catalogue 2003), Opti Pro (InVitrogen Ref 123094019, catalogue 2003), Episerf (InVitrogen Ref 10732422, catalogue 2003), Pro 293 S-CDM (Cambrex ref 12765Q, catalogue 2003), LC17 (Cambrex Ref BESP302Q), Pro CHO 5-CDM (Cambrex ref 12-766Q, catalogue 2003), HyQ SFM4-CHO (Hyclone Ref SH30515-02), HyQ SFM4-CHO-Utility (Hyclone Ref SH30516.02), HyQ PF293 (Hyclone ref SH30356.02), HyQ PF Vero (Hyclone Ref SH30352.02), Ex cell 293 medium (JRH Biosciences ref 14570-1000M), Ex cell 325 PF CHO Protein free medium (JRH Biosciences ref 14335-1000M), Ex cell VPRO medium (JRH Biosciences ref 14560-1000M), Ex cell 302 serum free medium (JRH Biosciences ref 14312-1000M), Ex cell 65319 (JRH Biosciences), Ex cell 65421(JRH Biosciences), Ex cell 65625 (JRH Biosciences), Ex cell 65626 (JRH Biosciences), Ex cell 65627 (JRH Biosciences), Ex cell 65628 (JRH Biosciences), Ex cell 65629 (JRH Biosciences), gene therapy medium 3 (animal component free) (SIGMA-Aldrich, ref. G-9916) (hereinafter named G9916 medium).

According to the first preferred embodiment, the serum-free medium N° 1 and the serum-free medium N° 2 are the same medium.

According to a second preferred embodiment the serum-free medium N° 1 and the serum-free medium N° 2 have a different composition. For example, the serum-free medium N° 1 is Excell 65319 (SAFC Biosciences) and the Opti Pro medium (InVitrogen Ref 12309-019, catalogue 2003) may be the serum-free medium N° 2.

According to a preferred embodiment, the serum-free medium N° 1 is Ex cell 65319 (JRH Biosciences). According to a second preferred embodiment, the serum-free medium N° 1 is Ex cell 65421 (JRH Biosciences).

According to a preferred embodiment, the serum-free medium N° 2 is Ex cell 65319 (JRH Biosciences). According to a second preferred embodiment, the serum-free medium N° 2 is G9916 (SIGMA-Aldrich).

The process of the invention encompasses the removal of the whole or a part of serum-free medium 1, followed by its replacement by serum-free medium N° 2. However, it is more convenient to remove a substantial fraction (e.g., up to about 50%) of the serum-free medium 1 and then replenish it with the serum-free medium N° 2 while still removing medium 1, e.g., through the spinfilter. According to a preferred embodiment, serum-free medium N° 2 is directly added to serum-free medium N° 1 without removal of a part of serum-free medium N° 1. Between 0.25 to 10 volumes of serum-free medium N° 2 is added to 1 volume of serum-free medium N° 1. In a preferred embodiment, between around 0.5 to 8 volumes of serum-free medium N° 2 is added to 1 volume of serum-free medium N° 1. In a more preferred embodiment, between around 3 to 6 volumes of serum-free medium N° 2 is added to 1 volume of serum-free medium. N° 1.

The serum-free medium N° 1 and/or the serum-free medium N° 2 is/are supplemented with at least one ingredient selected from the group consisting of amino-acids, lipids, fatty acids, cholesterol, carbohydrates, protein hydrolyzates of non-animal origin, and a mixture thereof.

Alternatively, the process of the invention is a fed-batch process that comprises the additional step of feeding the cells with at least one ingredient selected from the group consisting of amino-acids, lipids, carbohydrates, protein hydrolyzates of non-animal origin, surfactant and a mixture thereof. According to a first preferred embodiment, the feeding occurs during steps a) to d), alternatively only during the steps b) to d), or alternatively only during the steps d). The feeding may occur either on a daily basis or on a continuous basis. When the feeding is discontinuous, the feeding may occur one time per day, more than one time per day, or less than one time per day.

The SFM media of the invention comprise a number of ingredients, including amino acids, vitamins, organic and inorganic salts, sources of carbohydrate, each ingredient being present in an amount which supports the cultivation of a cell in vitro. However, in order to improve cell growth or viral productivity, additional ingredients are added to SFM media.

The choice of amino-acid(s) to add to the cell culture may be determined be an analysis of amino-acids consumption by the cells in the culture. According to a preferred embodiment, the amino-acids added to the medium are selected from the group consisting of asparagine and glutamine, or a mixture thereof. In a more preferred embodiment, glutamine is added, and the feeding of glutamine is performed during step a) to d) to maintain the glutamine concentration in the medium between around 0.5 mM to around 5 mM, preferably between around 1 mM to around 3 mM, and most preferably around 2 mM. In a preferred embodiment, the feeding of glutamine occur on a continuous basis.

According to a preferred embodiment, the carbohydrates added to the medium are selected from the group consisting of D-glucose, D-sucrose and D-galactose or a mixture thereof. According to a more preferred embodiment, the carbohydrate added is D-glucose. The feeding of D-glucose is performed during step a) to d), more preferably between b) to d) to maintain the D-glucose concentration in the medium between around 0.5 g/l to 25 g/l of D-glucose, preferably between around 1 g/l to 10 g/l of D-glucose, preferably around 2 to 3 g/l of D-glucose. In a preferred embodiment, the feeding of D-glucose occur on a continuous basis.

According to a preferred embodiment, the lipids are selected from the group consisting of cholesterol, steroids, and fatty adds such as palmitic acid, palmitoleic acid, stearic acid, oleic acid, linoleic acid, linolenic acid, and their derivatives, or a mixture thereof. More preferably the fatty acids are from SIGMA-ALDRICH (Ref. F7050) and around 0.35 ul/ml of fatty acids solution is added to the culture medium.

According to a preferred embodiment, the protein hydrolyzates of non-animal origin are selected from the group consisting bacteria tryptone, yeast tryptone, plant hydrolyzates, such as soy hydrolyzates, or a mixture thereof. In a preferred embodiment, the protein hydrolyzates of non-animal origin is yeast hydrolyzate.

The term "hydrolysate" includes an enzymatic digest of soy peptone or yeast extract The hydrolysate can be obtained from a plurality of soy peptone or yeast extract preparations, respectively, which can, be further enzymatically digested (for example, by papain), and/or formed by autolysis, thermolysis and/or plasmolysis. Hydrolysates also may be obtained commercially, such as Yeastolate, Hy-Soy, Hy-Yeast 412 and Hi-Yeast 444, from sources such as JRH BioSciences (Lenaxa, Kans.), Quest International (Norwich, N.Y.), OrganoTechnie S. A. (France) or Deutsche Hefewerke GmbH (Germany). Sources of yeast extracts also are disclosed in WO 98/15614. Sources of yeast extracts and soy hydrolysates also are disclosed in WO 00/03000. The hydrolysates used in media of the invention are preferably purified from a crude fraction, because impurities which could interfere with efficient cultivation are preferably eliminated during this purification, thereby improving the consistency of the hydrolysate. Purification can be by ultrafiltration or Sephadex chromatography (for example, with Sephadex G25 or Sephadex G10 or equivalent materials), ion-exchange chromatography, affinity chromatography, size exclusion chromatography or "reversed-phase" chromatography. Preferably, purification is performed by ultrafiltration utilizing a 10 kDa cut-off filter. These processes are known in the field. Using these methods, fractions can be selected which contain soy or yeast hydrolysate of defined molecular weight. Preferably, the average molecular weights of the soy and yeast hydrolysates are preferably between about 220 and 375 daltons.

Preferably, yeast hydrolyzate is present in the cell culture medium. Yeast hydrolyzate 50× (around 200 g/l) obtained for example from JRH-BIOSCIENCES (Ref 58902) is present in the cell culture medium at a final concentration comprises between around 0.1× to 2×, preferably around 0.5× to around 1× into the culture medium. Soy hydrolyzate may also be added to the cell culture medium. Soy hydrolyzate 50× obtained for example from JRH-BIOSCIENCES (Ref 58903100M) is added at a final concentration comprises between around 0.1× to 2×, preferably around 1× into the culture medium. Alternatively a mixture of soy hydrolyzate and yeast hydrolyzate may be added to the cell culture medium as described in US 2004/0077086.

The medium may contain auxiliary substances, such as buffer substances like sodium bicarbonate, oxidation stabilizers, stabilizers to counteract mechanical stress, or protease inhibitors. If required, a non-ionic surfactant, such as polypropylene glycol (PLURONIC F-61, PLURONIC F-68, SYNPERONIC F-68, PLURONIC F-71 or PLURONIC F-108) can be added to the medium as a de-foaming agent. These agents are generally used to protect cells from the negative effects of aeration since, without an addition of a surfactant, the ascending and bursting air bubbles can lead to damage of those cells that are located on the surface of these air bubbles ("sparging"). The quantity of nonionic surfactant is preferably between about 0.05 and about 10 g/L, typically between about 0.1 and about 5 g/L. According to another embodiment of the invention, the concentration of surfactant in cell culture medium may be decrease to enlarge the size of the cell clumps.

According to an embodiment of the invention, the addition of serum-free medium N° 2 to the cell culture, is performed after infection step b), preferably between around 0.5 to 4 hour after step b), and more preferably around 1 hour after step b). According to another embodiment of the invention, the addition of serum-free medium N° 2 to the cell culture, is performed before infection step b), preferably between around 0.5 to 4 hour after step b), and more preferably around 1 hour before step b). According to another embodiment of the invention, the addition of serum-free medium N° 2 to the cell culture, is performed simultaneously to infection step b.

The viral infection of step b) is carried out at an m.o.i (multiplicity of infection) of about 10 to $10^{-6}$, preferably about $10^{-2}$ to $10^{-5}$, and more preferably about $10^{-4}$. The man skilled in the art will determine the optimal m.o.i according to the virus type.

In step c), the infected cells are preferably cultured during at least 24 h, at least 48 h, at least 72 h, at least 96 h, at least 120 h, at least 144 h. When the virus is a poxvirus, the infected cells are cultured at least 144 h.

In the process of the invention, the cell culture of step a) is carried out by batch culture, repeated batch culture, fed-batch culture or perfusion culture. More preferably, the cell culture of step a) is performed by fed-batch culture. The infection in step b) is performed when the cell density is at least around 4 million, preferably 6 million cells/ml, more preferably 8 million cells/ml in batch or fed-batch process. When a perfusion process is used, the infection in step b) is performed when the cell density is of at least at least 8 million cells/ml, preferably around 9 to 10 million cells/ml, or even higher.

The pH of the serum-free culture medium in steps a), b), c) and d) is preferably monitored by the bioreactor. The pH shall be in a range from 6.5 to 7.8, preferably around 6.8 to 7.5, and more preferably around 7.2.

In the process of the invention, step d) lasts for 2 to 10 days before the harvest. According to a preferred embodiment, step d) lasts for 3 to 7 days before the harvest.

The cell culture is performed at a temperature comprises between 32° C. to 39° C. depending of the virus type. For influenza virus production, cell culture infection is preferably performed at 33° C.

EBx® cells have the ability to grow in suspension culture with cells clumped in loose aggregates of few cells, up to more than hundred(s) of cells. Without to be bind by a theory, the size of the dumps may vary according to the composition of cell culture medium. For example, presence of surfactant such as polypropylene glycol (PLURONIC F-61, PLURONIC F-68, SYNPERONIC F-68, PLURONIC F-71 or PLURONIC F-108) and the stirring may have an effect on the clumps size. The inventor has now found that the viral yield may be increased by allowing the EBx® cells of the invention to aggregate to each others to form dumps during at least step a) of the process. During the scaling-up from the master and working cell bank vial through the various sizes of T-flasks or roller-bottles to bioreactors, the suspension cells are generally passaged to a larger vessel, either by dilution into fresh medium or by centrifugation followed by a re-suspension of cell pellet into a fresh medium. The inventor has found that during the cells passages, it is recommended to keep large cell clumps into the culture. To do so, it is better not to disrupt cells clumps in order to improve the replication of virus in EBx® cells. For example, during the initial phases of culture of step a) in T-flasks or roller-bottles, it is recommended to dilute the cell culture to passage the cells into larger vessel(s), and it is not recommended to centrifuge, nor to disrupt the cells clumps by pipetting or stirring. However, too large clumps may be suboptimal for a high viral production. Consequently, the man skilled in the art will define whether a partial disruption of the dumps, by pipetting or stirring, during initial cell passages of step a) may improve viral yield. According to a preferred embodiment, poxviruses, and preferably MVA, ALVAC and Fowlpox viruses are obtained by a process of the invention that include the step a) of proliferating clumped EBx® in loose aggregates of few cells, up to more than at least one hundred of cells, at least two hundred of cells, at least five hundred of cells, at least thousand(s) of cells.

The instant invention is also appropriate to other cell types used to propagate viruses, such as without limitation, chicken embryonic fibroblasts (CEFs), VERO cells, PerC6, MDCK, and that are able to grow in suspension as cell clumps.

The invention also relate to the virus obtainable by a process of the invention.

The instant invention also relates to the vaccine containing the virus of the invention. The process of manufacturing a viral vaccine comprises the process of replicating a virus according to the invention wherein the step e) of virus harvest is comprising at least one step selected among filtering, concentrating, freezing and stabilizing by addition of stabilizing agent. The virus harvest is performed according to technologies well-known to the man skilled in the art. According to a preferred embodiment, the step of harvesting said virus comprises collecting cell culture supernatant obtained from centrifugation of cell culture, then filtering, concentrating, freezing and stabilizing virus preparation by addition of stabilizing agent. For example, for influenza virus see Furminger, In Nicholson, Webster and Hay (Eds) Textbook of influenza, chapter 24 pp 324-332.

The process of manufacturing a viral vaccine according to the invention may also comprise the additional step of inactivation of harvested virus. Inactivation is preferably performed by treatment with formaldehyde, beta-propiolactone, ether, ether and detergent (i.e. such as Tween 80™), cetyl-trimethyl ammonium bromide (CTAB) and Triton N102, sodium deoxycholate and tri(N-butyl)phosphate.

According to another embodiment, the invention also relates to a process of preparation of viral antigenic proteins from the virus obtainable by a process of the invention, said process comprises the additional steps of:
  a) optionally, incubating cell culture supernatant comprising whole virus with a desoxyribonucleic acid restriction enzyme, preferably DNAses (see EC3.1.21 and EC3.1.22 classification) and nucleases (see EC3.1.30 and EC3.1.31 classification). Preferably, DNA digestion enzyme is benzonase (Benzon nuclease) or DNase I;
  b) adjunction of cationic detergent. Examples of cationic detergent are; without limitation: cetyl-trimethyl ammonium salt such as CTAB, myristyl-trimethyl ammonium salt, lipofectine, DOTMA and Tween™;
  c) Isolation of antigenic proteins. This latter step may be realized by centrifugation or ultrafiltration.

The virus in the vaccine may be present either as intact virus particles, or as disintegrated virus particles. According to an embodiment, the vaccine is a killed or inactivated vaccine. According to another embodiment, the vaccine is a live attenuated vaccine wherein said vaccines mainly comprises EBx cell culture supernatant obtainable by the process of the invention, preferably without serum, optionally filtered and/or concentrated and comprising said virus. According to a third embodiment, the vaccine is comprising viral antigenic proteins obtainable from a virus prepared according to the process of the invention.

The invention also pertain to provide a vaccine comprising an infected cell line EBx®, preferably EB14, obtainable by the process of the invention, and wherein infected cell line EBx®, preferably EB14, are harvested in step d).

The vaccine of the invention may comprise the virus of the invention in combination with pharmaceutically acceptable substances which increase the immune response. Non limitating examples of substances which increase the immune response comprises incomplete Freund adjuvant, saponine, aluminium hydroxide salts, lysolecithin, plutonic polyols, polyanions, peptides, bacilli Calmette-Guerin (BCG) and *corynebacterium parvum*. Example of synthetic adjuvant is QS-21. In addition, immuno-stimulating proteins (interieukins Il1, Il2, IL3, IL4, IL12, IL13, granulocyte-macrophage-colony-stimulating factor, . . . ) may be used to enhance the vaccine immune response.

The vaccine of the invention is preferably a liquid formulation, a frozen preparation, a dehydrated and frozen preparation, optionally adapted to intra-nasal route of administration.

The vaccine of the invention is preferably use for the prophylactic and/or therapeutic treatment of a human infected by a virus selected among smallpox and influenza, measles, mumps and rubella viruses. The recombinant viral vaccine of the invention may also be used for the prophylactic and/or therapeutic treatment of chronic diseases such as cancer or infectious diseases, such as AIDS.

The EBx® cell lines of the invention are useful to generate and produce re-assorted virus. The virus with a segmented genome, such as influenza virus may be re-assorted. When infecting simultaneously EBx® cells of the invention with at least two different strains of influenza virus, a mix of segmented genome from two different strains is present in the same host cell. During virus assembly, all combination of genomic segments can theoretically be generated. Specific reassorted virus may thus be isolated by selecting or eliminating, with an antibody for example, virus with a desired traits (See Kilnourne E. D in Plotkin S A and Mortimer E. A. Eds, Vaccines 1994).

The EBx® cell lines of the invention are also useful to generate and produce influenza virus by reverse genetics (See Enami, Proc. Natl. Acad. Sd. USA 87:3802-3805 (1990); Enami et Palese, J. Virol. 65:2511-2513 (1991); Luytjes, *Cell* 59:1107-1113 (1989)).

The invention also relates to the diagnostic composition containing viruses of the invention or constituents thereof.

The examples below explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims. For the remainder of the description, reference will be made to the legend to the figures below.

FIGURES

FIG. 1: Transmission Electronic Microscopy analysis of EB14 cells

EB14 cells display a typical embryonic stem cells morphology (i.e. high nucleo-cytoplasmic ratio) that resemble the phenotype of murine embryonic stem cells (mES). EB14 cells are small round cells with a large nucleus and nucleolus with short pseudopodia extending from the plasma membrane. They are highly metabolically active with a ribosome and mitochondria rich cytoplasm. The cell morphology of EB14 cells is different to the one of chicken embryonic fibroblasts (CEF).

FIG. 2: Karyotyping analysis of EB14 cells at passages 105 and 118

Analysis of EB14 cells cultured in serum-free medium until passages 105 and 118 confirmed the diploid nature of the cells, with the presence of 18 macro-chromosomes and 30 micro-chromosomes (upper, panel). This result is in agreement with the chromosome numbers expected for chicken cells (lower panel).

FIG. 3: Telomerase expression in EB14 cells

Telomerase expression in EB14 cells cultured in serum-free medium at different passages was investigated by using Roche telomerase detection kit (Telomerase OCR ELISA). Telomerase is found to be highly expressed in EB14 cells. The high level of telomerase expression is maintained over passages as shown at passage 89, at passage 160 (which correspond to EB14 cell Master Cell Bank), and at passage 179 (which correspond to end of production passages). Canine MDCK cell line are used a negative control and do not express telomerase. Similar absence of telomerase expression was found for CEFs cells (Data not shown).

FIG. 4: ENS1 gene is expressed in EB14 cells

The ENS1 gene was described as being specifically expressed in chicken ES cells (Acloque & al., Mech Dev. 103, p 79-91, 2001). Its expression in EB14 cells was evaluated by RT-PCR. Avian embryonic stem cells (ES cells), avian embryonic cells collected at oviposition and EB14 cells at various passage (P21, P159, P160) are found to strongly express ENS1 gene while avian cell line DF1 (U.S. Pat. No. 5,672,485) and chicken embryonic fibroblasts (CEFs) do not express this gene. Analysis of the housekeeping GAPDH gene is performed in parallel on the same samples to control the presence of the RNAs (lower panel).

Figure 5:
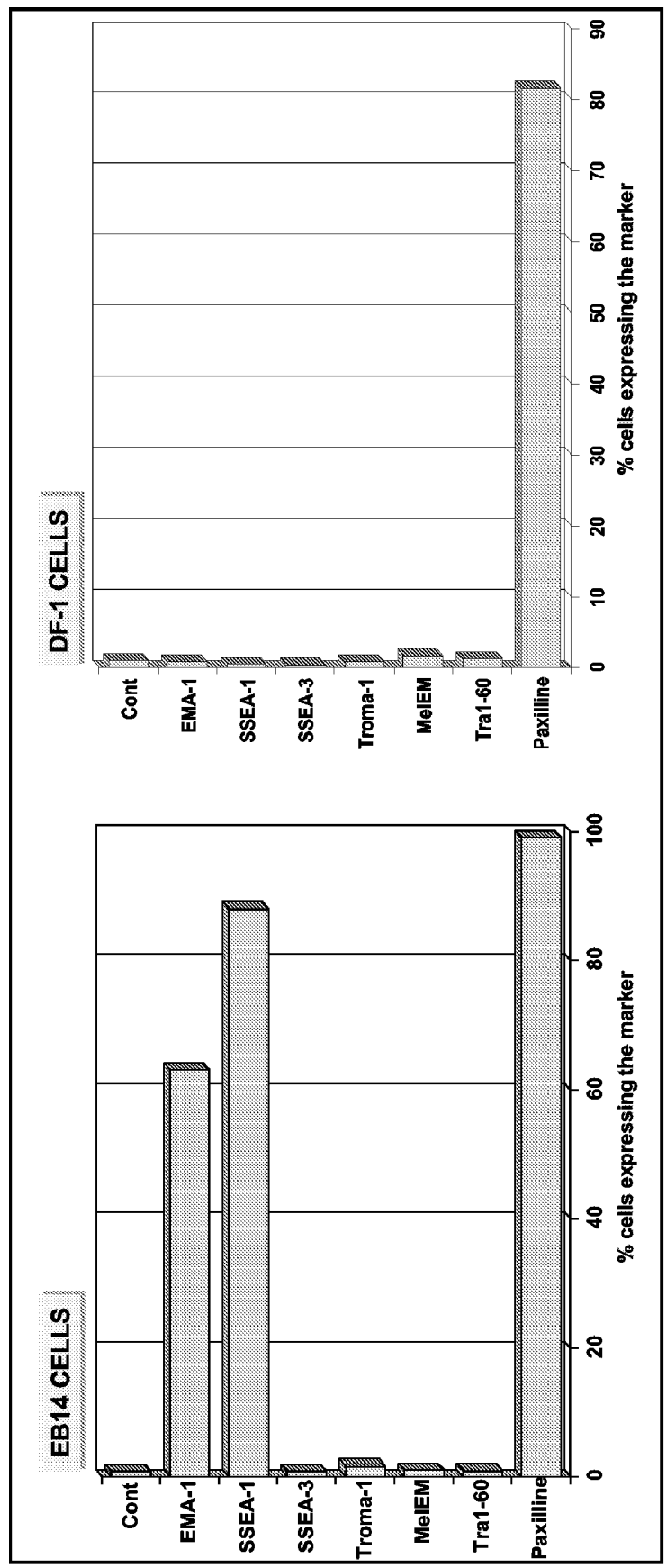

FIG. 5: Expression of ES cell-specific markers in EB14 cell line (left panel) and DF1 cell line (right panel)

EB14 cells express EMEA1 and SSEA1 genes while DF1 cell does not. Paxiline gene is an ubiquitous gene used as a control. EB14 cells do not express cell markers TROMA-1, MelM, TRA-1-60 and SSEA3.

Figure 6:
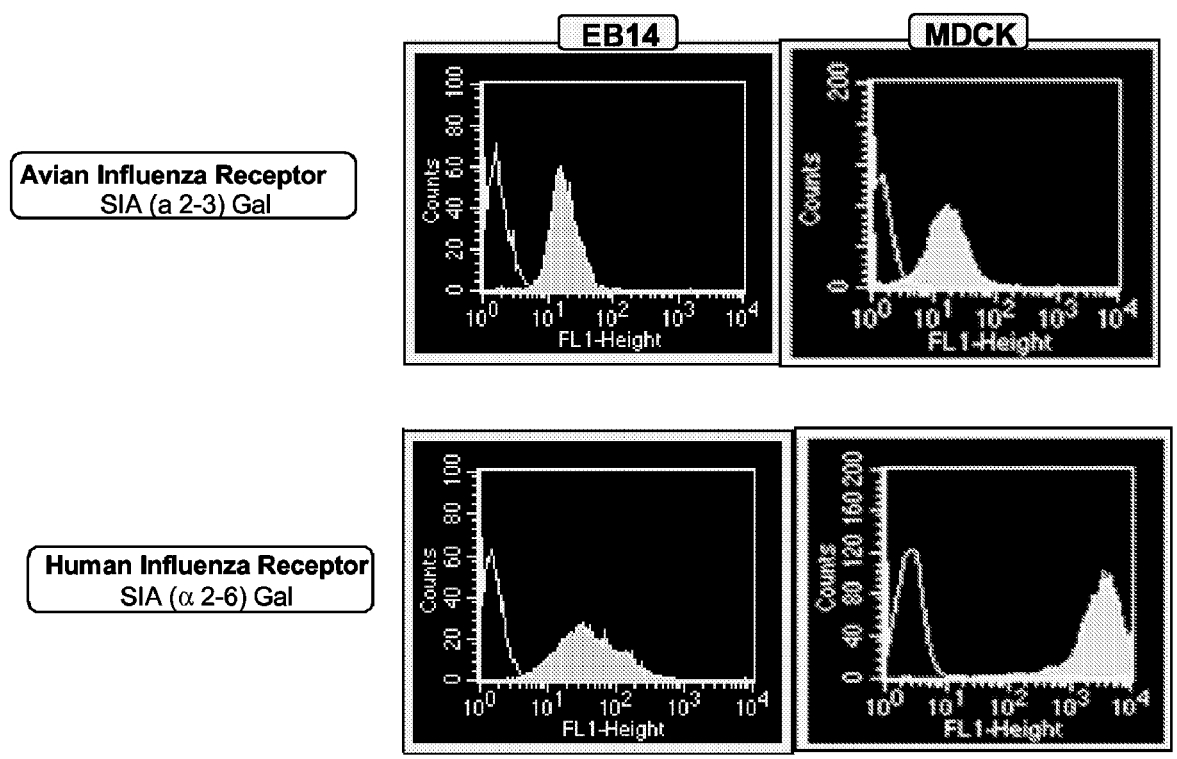

FIG. 6: Cell surface expression of receptors SA 2-3 and SAa2-6 in EB14 and MDCK cell lines Cells are incubated with digoxygenin labelled lectins: Sambuca nigra agglutinin lectin specifically binds to Sia2-6Gal, while Maackia amurensis agglutinin lectin specifically binds to Sia2-3Gal. Lectins that bind to cells are revealed with anti-digoxygenin antibody FITC-labelled according to well-known techniques by the man skilled in the art. FITC-labelled cells are numbered with a fluorescent cell sorter (FACS). SAα2-3 and SAa2-6 molecules are been described to be the receptors for the avian and human influenza viruses, respectively.

Figure 7A:
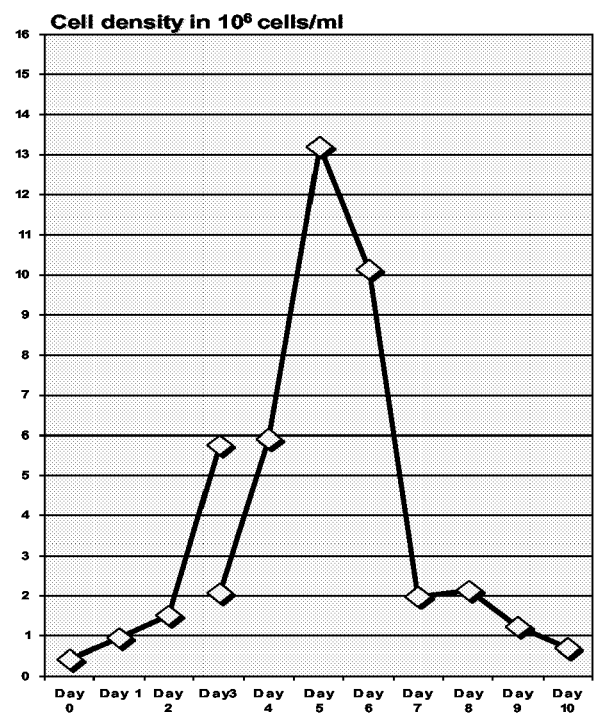
Figure 7B:
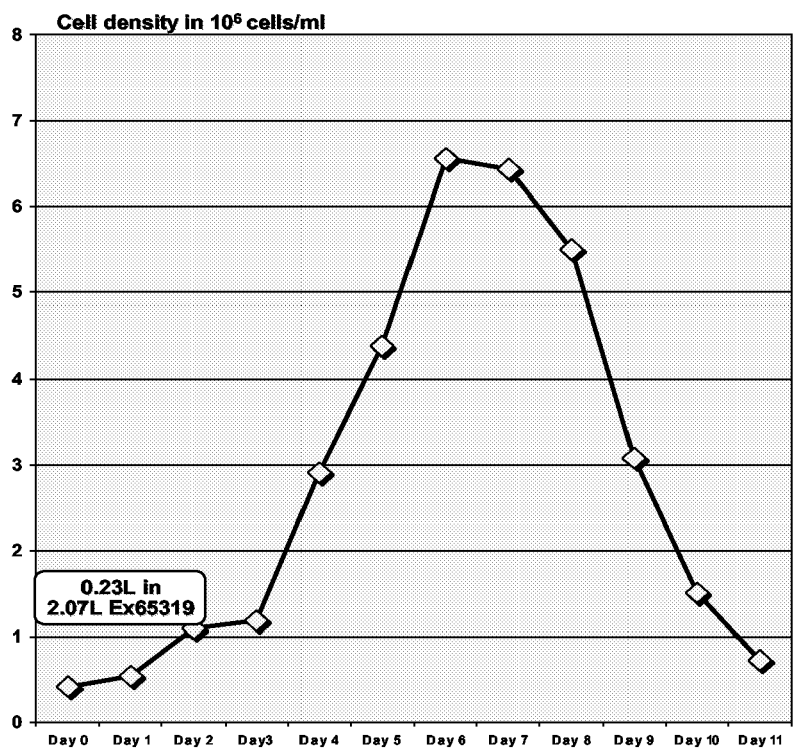

FIGS. 7A and 7B: Growth kinetics of EB14 cells in a 3 L-fedbatch bioreactor

FIG. 7A—EB14-derived biomass was allowed to accumulate at 37° C. in a cell growth medium supplemented with 0.5× yeastolate until a cell density of $5-6.10^6$ cells/mL was reached. Then the mixture was 2.9 fold diluted and cell growth kinetic was followed-up over a 10 days period. Cell density of 13 million cells/ml was reached at day 5.

FIG. 7B-Split ratio flexibility for cell growth kinetic of EB-14 cells in a 3 L fedbatch bioreactor Following a cell seeding with a split ration of 1/10 (0.23 L at a density of $0.4.10^5$ cells/mL in 2.1 L final volume), EB14-derived biomass was allowed to accumulate in Excell 65319 (SAFC) growth medium at 37° C. over a 11 days period. L-glutamine (2 mM) and D-(+)glucose (2 g/L) concentrations were daily adjusted as a fed-batch process, and bioreactor parameters were fixed as follows: rotation speed: 80 rpm, $PO_2$: 50%, pH: 7,20.

Figure 8:
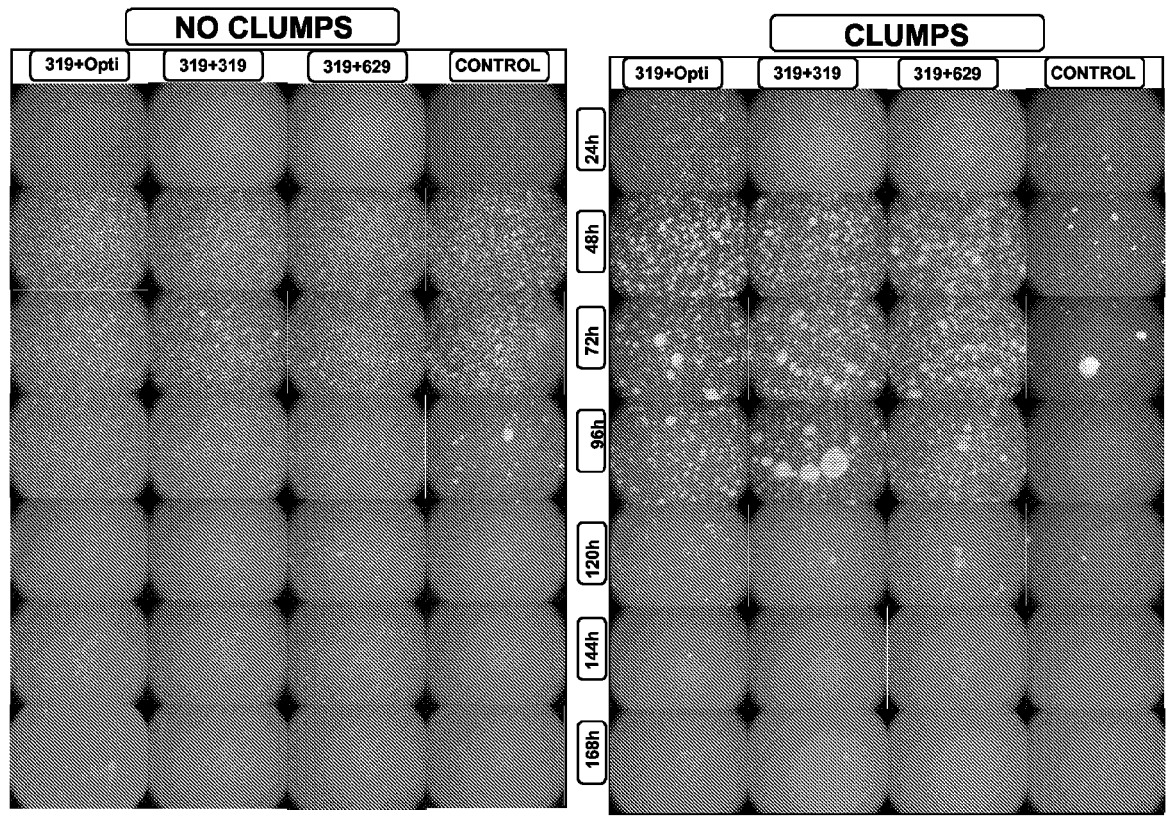

FIG. 8: Influence of production medium and clumps' size for MVA-GFP virus propagation in infected EB14 cells: GFP expression EB14 were allowed to form small (left panel) or large (right panel) dumps in T175 stirred tank flasks during cell proliferation in a cell growth SFM medium (SAFC: Excell 65319). Clumps were then infected with $10^{-2}$ $TCID_{50}$/cell of MVA-GFP virus and the mixture was diluted in several production SFM media (Optipro, Excell 65319, Excell 65629). During a 7 days virus propagation period at 37° C., pictures of UV-exposed infected cells were taken daily. Control: opbpro (INVITROGEN) was used as cell growth and production medium.

Figure 9:
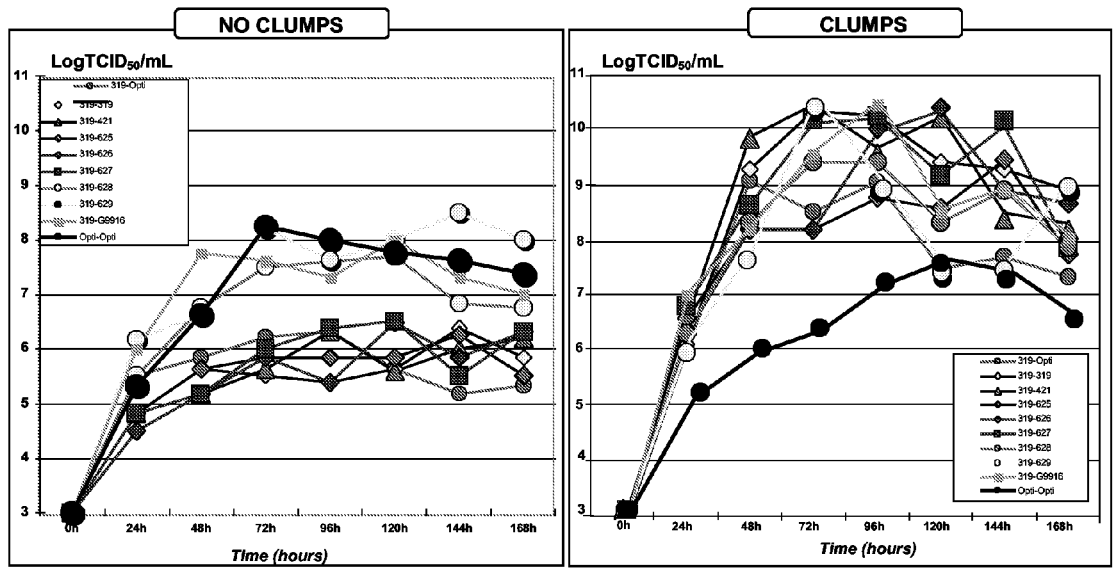

FIG. 9: Influence of production medium and clumps' size for MVA-GFP virus propagation in infected EB14 cells: infectious virus titration EB14 were allowed to form small (left panel) or large (right panel) dumps in T175 stirred tank flasks during cell proliferation in a cell growth medium (SAFC Excell 65319). Clumps were then infected with $10^{-2}$ $TCID_{50}$/cell of MVA-GFP virus and the mixture was diluted in several production media (Optipro, Excell 65319, Excell 65421, Excell 65625, Excell 65626, Excell 65627, Excell 65628, Excell 65629, G9916). During a 7 days virus propagation period at 37° C., samples were collected daily and $TCID_{50}$ titration was performed at the end of the kinetic.

Figure 10:
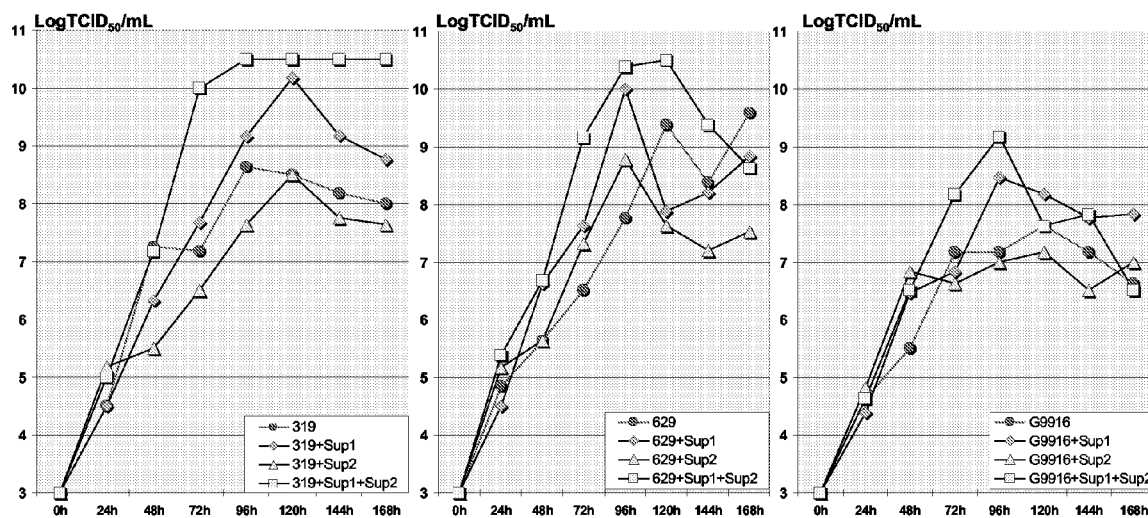

FIG. 10: Influence of production medium and supplements for MVA-GFP virus propagation in infected EB14 cells EB14 were allowed to form small dumps in T175 stirred tank flasks during cell proliferation in a cell growth medium (SAFC Excell 65319). Cells were then infected with $10^{-2}$ $TCID_{50}$/cell of MVA-GFP virus and the mixture was diluted in several production media (from left to the right panel: medium Excell 65319, Excell 65629 or G9916) supplemented or not with 1× yeastolate (supplement 1) and/or 1× fatty acid (supplement 2). During a 7 days virus propagation period at 37° C., samples were collected daily and $TCID_{50}$ titration was performed at the end of the kinetic.

Figure 11:
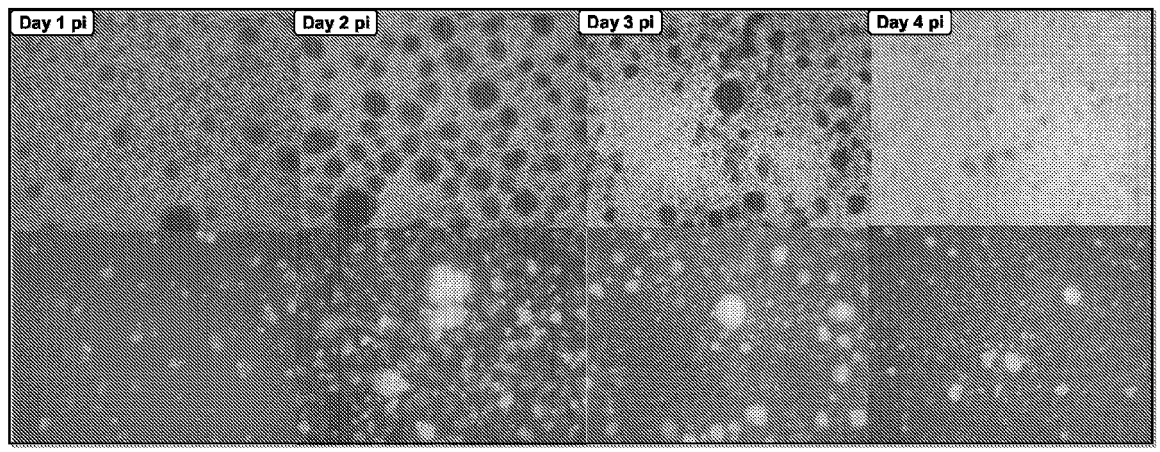

FIG. 11: GFP expression in EB-14 cells Infected with MVA-GFP virus in a 3 L fed-batch bioreactor EB14-derived biomass was allowed to accumulate during cell proliferation phase in Excell 65319 growth medium. Cells were then infected with $10^{-2}$ $TCID_{50}$/cell of MVA-GFP virus and the mixture was diluted in G9916 production medium. Pictures (magnification ×5 or ×10) of UV-exposed infected cells at 37° C. were then taken daily (PI: Post-infection).

Figure 12:
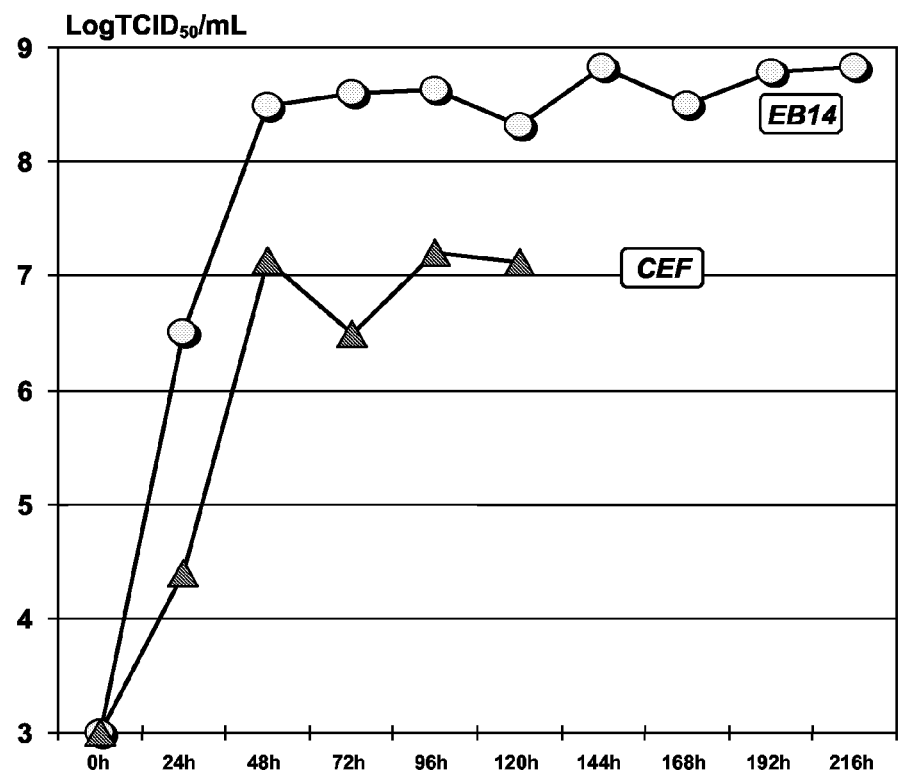

FIG. 12: Infectious virus titration of EB14-derived MVA-GFP Influenza virus propaged in a 3 L fed-batch bioreactor EB14-derived biomass was allowed to accumulate during cell proliferation phase in Excell 65319 growth medium. Cells were then infected with $10^{-2}$ $TCID_{50}$/cell of MVA-GFP virus and the mixture was diluted in Excell 65319 supplemented with 1×Yeastolate. During a 9 days virus propagation period at 37° C., samples were collected daily and TCID$_{50}$ titration was performed at the end of the kinetic and compared with titers obtained on CEF cells.

Figure 13:
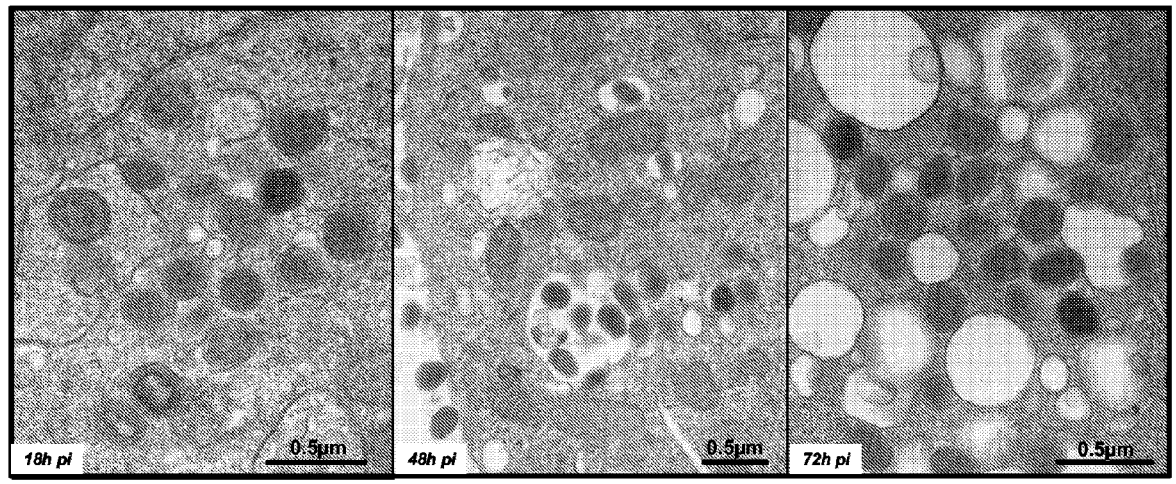

FIG. 13: Electron micrographs analysis of MVA-GFP virus produced on EB14 cells

EB14 were infected with $10^{-2}$ TCID/cell of MVA-GFP virus and harvested 18 h, 48 h and 72 h post-infection. Thin sections of fixed and embedded samples were examined by electron microscopy (Dr. D. Spehner, IGBMC, Strasbourg).

Figure 14:
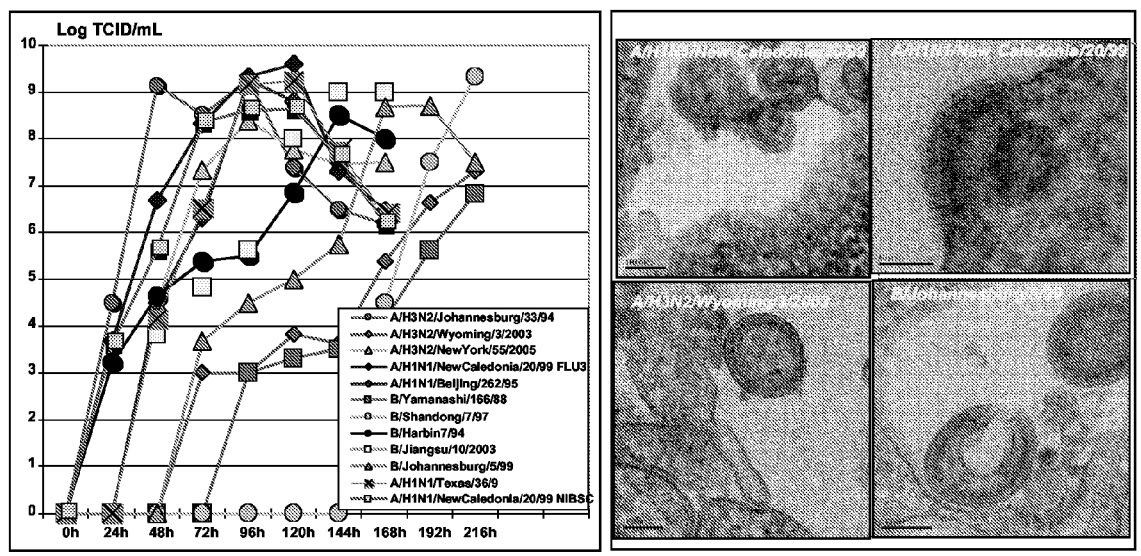

FIG. 14: Infectious virus titration of multiple human Influenza strains produced on EB14 cells EB14 cells were infected in T175 stirred tank flasks with $10^{-4}$ TCID$_{50}$/cell of various A/H$_3$N$_2$, A/H1N1 and B human influenza strains, in presence of 0.75 USP/mL of recombinant trypsin. Samples were collected every 24 h and TCID$_{50}$ titer was analyzed at the end of the kinetic by titration of MDCK cells in absence of bovine serum (left panel). Some infected EB14 cells were in parallel analyzed by electron microscopy, revealing the production of influenza virus particles (right panel; Dr. D. Spehner, IGBMC, Strasbourg).

Figure 15A:
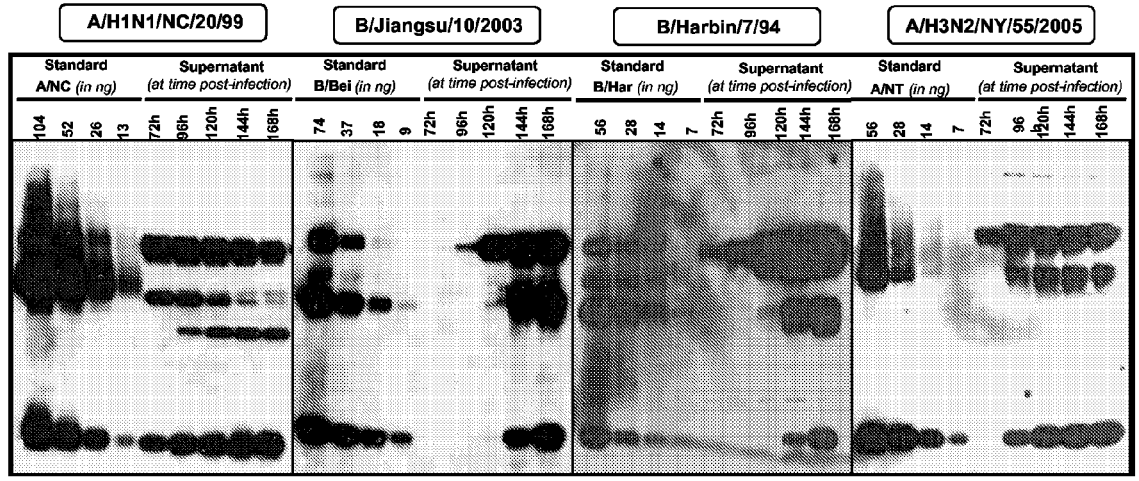
Figure 15B:
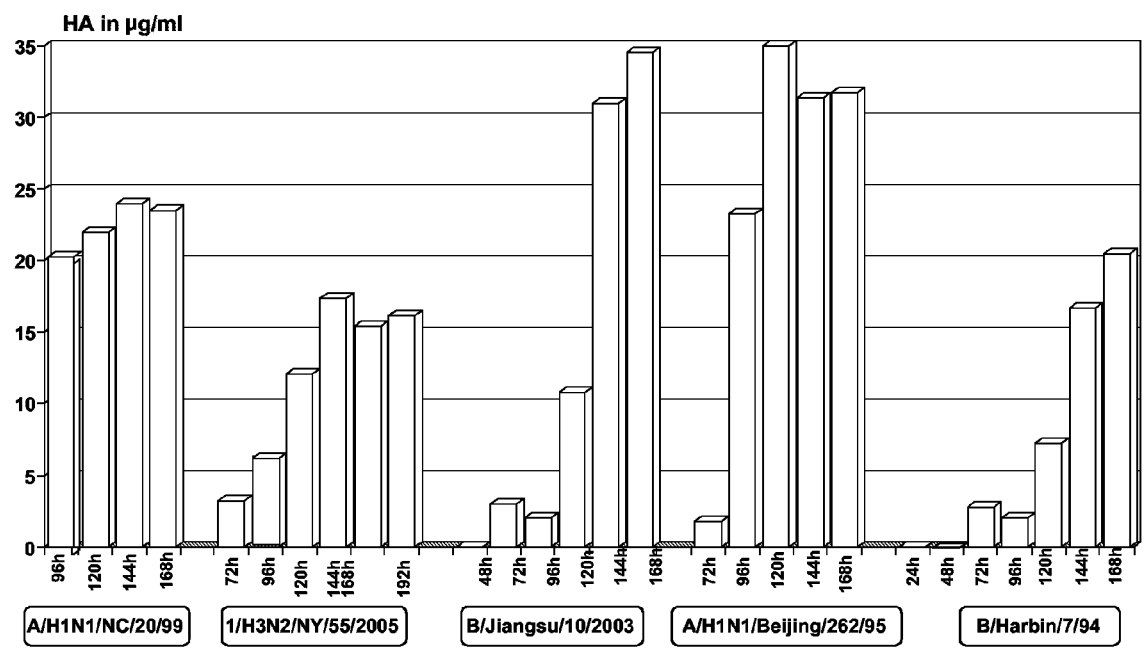

FIGS. 15A and 15B: Productive replication of multiple Influenza virus strains in EB14 cells FIG. 15A—Western blot analysis of haemagglutinin (HA) in EB14 cells infected with various Influenza virus strains EB14 cells are cultured in serum-free medium in T175 shaken flasks and are infected with the indicated viral strains at a multiplicity of infection of $10^{-4}$, in presence of 0.75 USP/mL of trypsin. 4 μL of cell culture supernatants are collected daily and analyzed by electrophoresis through a 10% SDS-PAGE and western-blotting. Proteins were electroblotted to polyvinylidene difluoride membrane and uncleaved (HA0) or post cleavage subunits (HA1 and HA2) of HA were detected by incubation with specific polyclonal anti-HA sheep serum. An anti-sheep-IgG conjugated to peroxydase was used for immunostaining. For each virus strain, HA accumulation from 72 h to 168 h post-infection is compared with increasing amounts of egg-derived standard HA reagents.

FIG. 15B—SRID analysis of EB14-derived HA production levels for various Influenza viruses EB14 cells were infected in T175 shaken flasks with $10^{-4}$ TCID$_{50}$/cell of various A/H3N2, A/H1N1 and B human influenza strains, in presence of 0.75 USP/mL of trypsin. Samples were collected every 24 h and Serial Radial immunodiffusion (SRID) analysis was performed at the end of the kinetic. For each virus strain, calculation of HA accumulation is related to a dose-response curve of well-defined corresponding standard antigens.

Figure 16A:
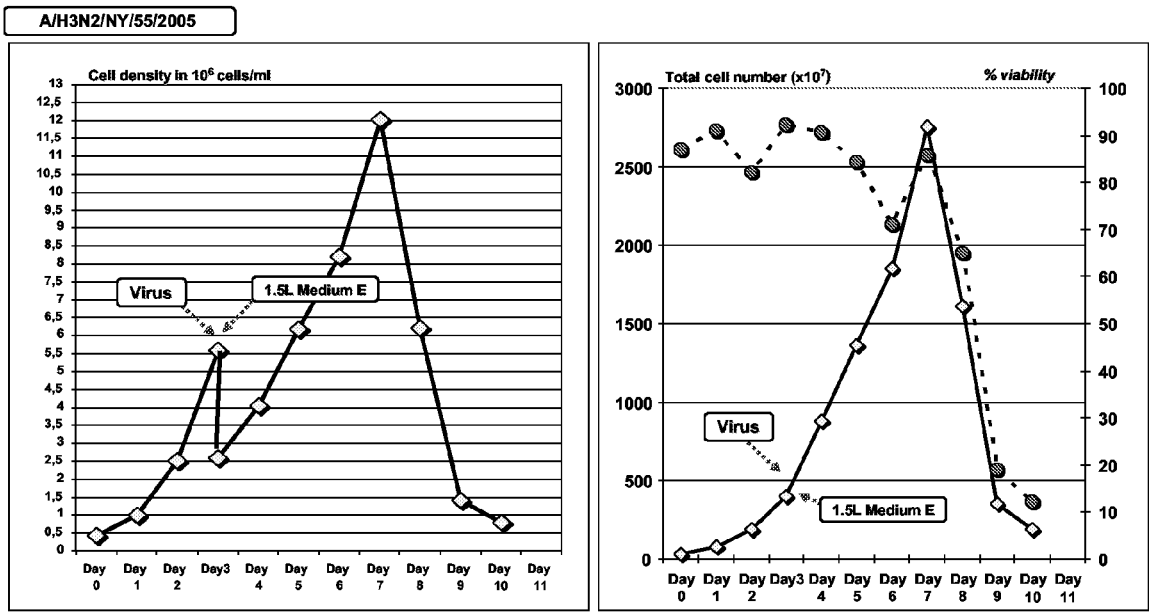
Figure 16B:
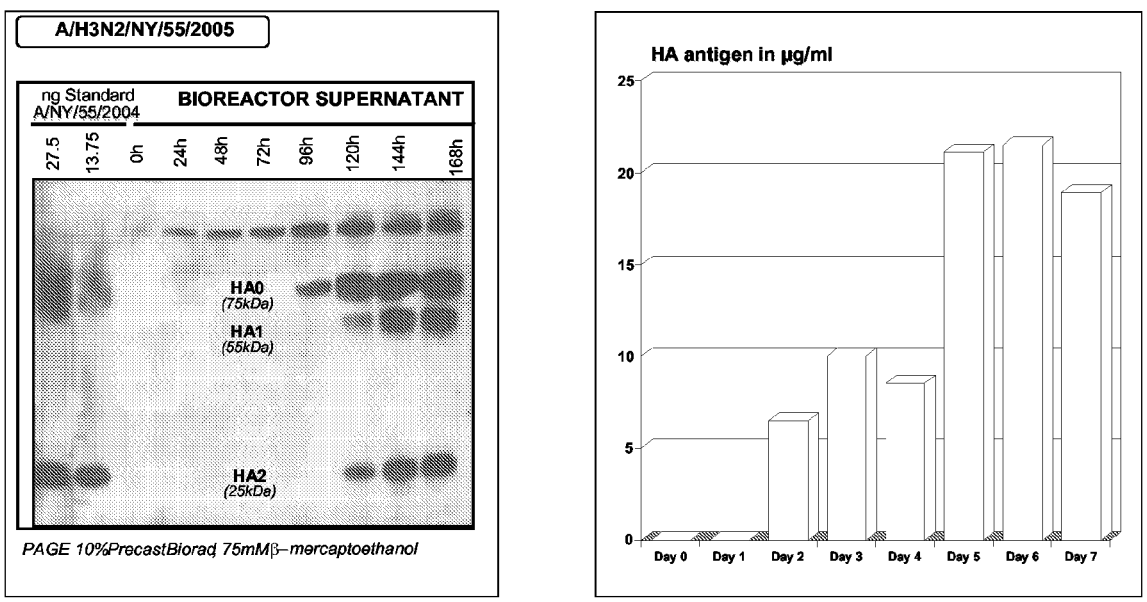

FIGS. 16A and 16B: Production of A/H3N2 influenza virus strains in EB14 cells in 3 L-bioreactors FIG. 16A—Growth kinetic of EB14 cells infected with A/H3N2/NewYork/55/2005 Influenza virus strain EB14 biomass was allowed to accumulate at 37° C. during cell proliferation phase in a cell growth medium. Cells were then infected with $10^{-4}$ TCID$_{50}$/cell of A/NH3N2/New York/55/2005 influenza virus, the mixture was diluted in Excell65629 production medium (medium E) supplemented with 0.3 USP/mL of trypsin and temperature was lowered to 33° C. During a 10 days virus propagation period, samples were collected daily and stored at 80° C. Left panel: cell density (×10$^6$ cells/mL), right panel: total cell number (yellow rhombus, ×10$^7$ cells) and viability (red circles, %).

FIG. 16B—Analysis of HA by western-blot and SRID assays

Samples collected from the 3 L bioreactor over a 7 days post-infection period were analyzed for detection and quantification of produced HA with a specific polyclonal anti-HA sheep serum. Left panel: western blot analysis of 4 μL of viral supernatant were immunostained with an anti-HA sheep antibody together with an anti-sheep-IgG conjugated to peroxydase. HA accumulation is compared with increasing amounts of egg-derived standards reagents. HA0: uncleaved HA subunit, HA1&HA2: cleaved HA subunits. Right panel: SRID quantification of 10 μL of viral supernatant. Calculation of HA content is related to a dose-response curve of the same standard reagents.

Figure 17A:
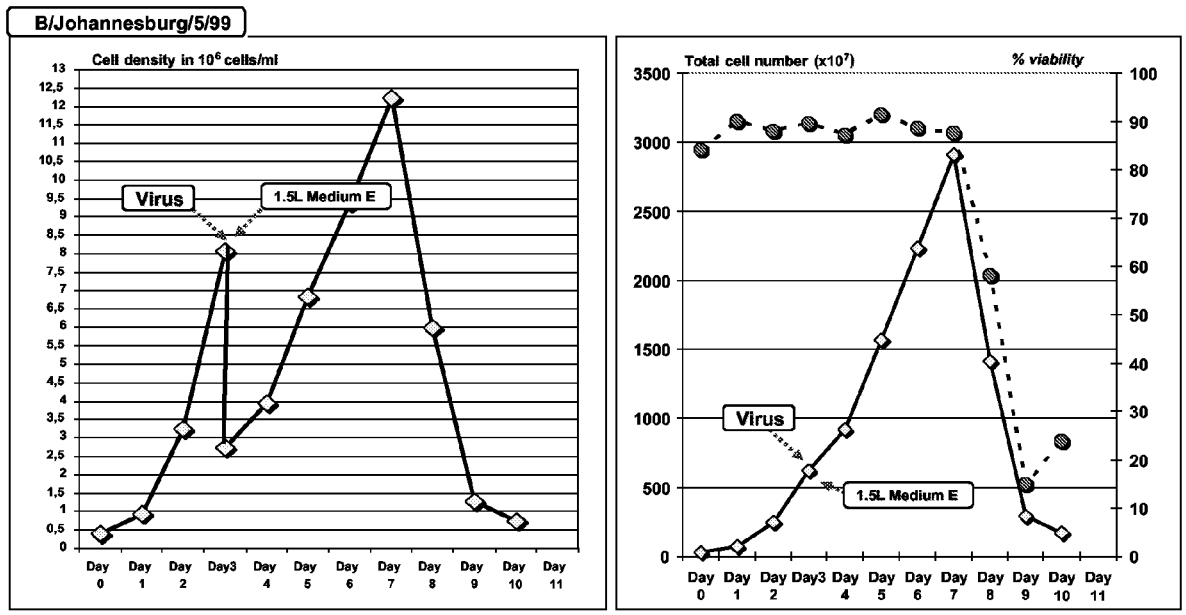
Figure 17B:
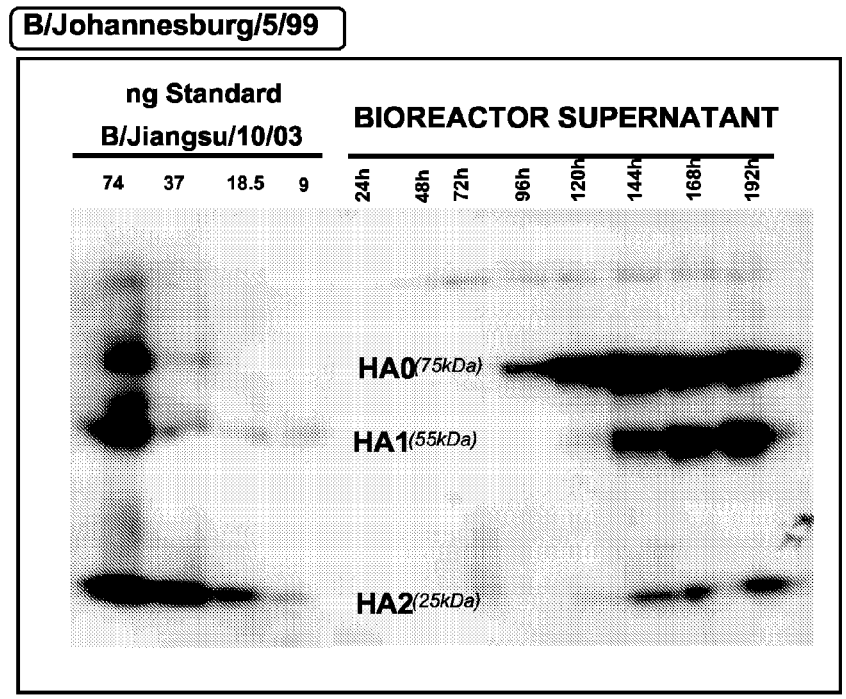

FIGS. 17A and 17B: Production of B Influenza virus strain in EB14 cells in 3 L-bioreactor FIG. 17A—Growth kinetic of EB14 cells Infected with B/Johannesburg/5/99 influenza virus strain EB14 cells were allowed to accumulate at 37° C. during cell proliferation phase in a cell growth medium. Cells were then infected with $10^{-4}$ TCID$_{50}$/cell of B/Johannesburg/5/99 influenza virus, the mixture was diluted in SAFC Excell 65629 production medium (medium E) supplemented with 0.3 USP/mL of trypsin and temperature was lowered to 33° C. During a 10 days virus propagation period, samples were collected daily and stored at −80° C. Left panel: cell density (×10$^6$ cells/mL), right panel: total cell number (yellow rhombus, ×10$^7$ cells) and viability (red circles, %).

FIG. 17B—Western blot analysis of EB14-derived B/Johannesburg/5/99 influenza virus HA Samples collected over a 7 days post-infection period were analyzed for detection of produced HA with a specific polyclonal anti-HA sheep serum. 4 μL of viral supernatant were used to perform the western blot analysis, where antigens-captured antibodies were immunostained with an anti-sheep-IgG conjugated to peroxydase. HA accumulation is compared with increasing amounts of egg-derived standards antigens. HA0: uncleaved HA subunit, HA1&HA2: cleaved HA subunits.

Figure 18A:
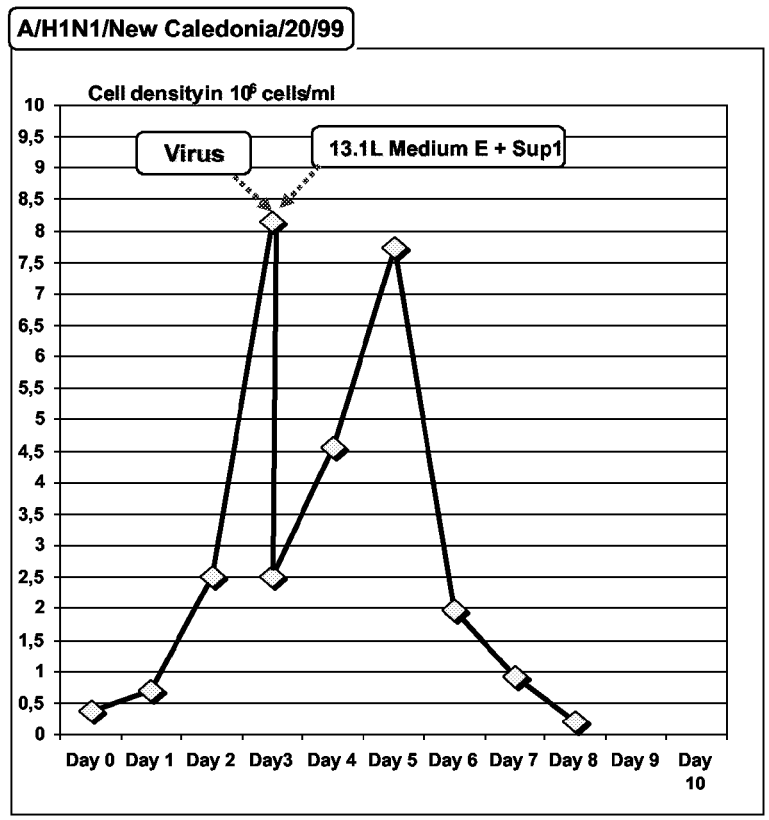
Figure 18B:
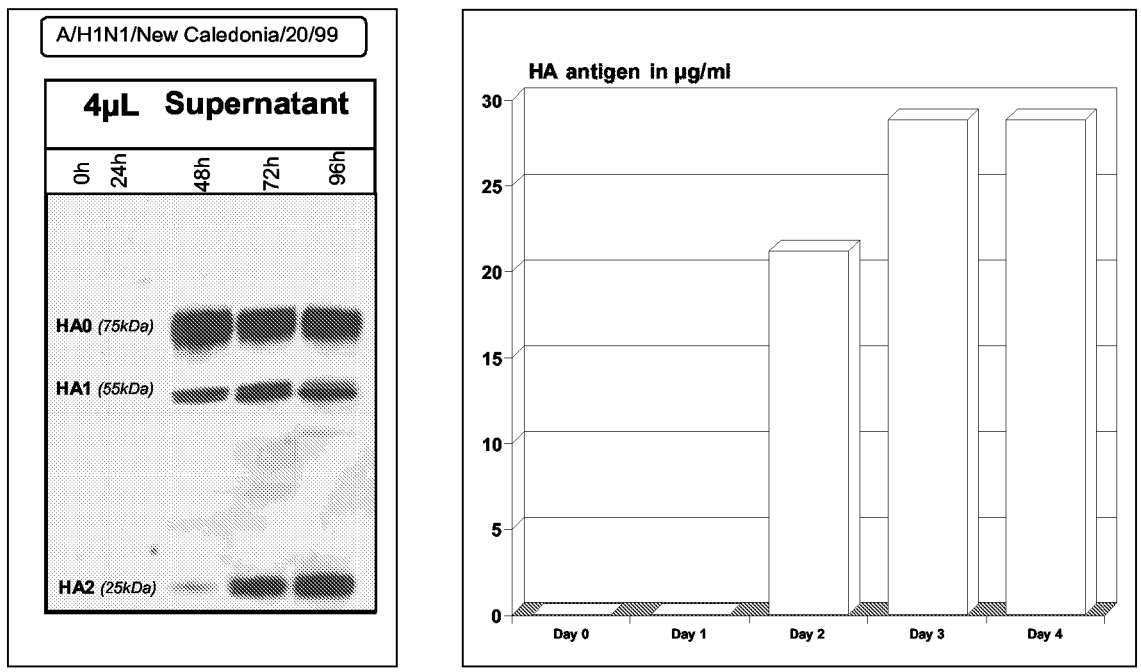

FIGS. 18A and 18B: Production of A/H1N1 Influenza virus strains in EB14 cells in 30 L-bioreactor FIG. 18A—Growth kinetic of EB14 cells infected with A/H1N1/NewCaledonia/20/99 influenza virus strain EB14 cells were allowed to accumulate at 37° C. during cell proliferation phase in a cell growth medium. Cells were then infected with $10^{-4}$ TCID$_{50}$/cell of A/H1N1/NewCaledonia/20/99 influenza virus, the mixture was diluted in SAFC medium Excell 65629 production medium (medium E) supplemented with 0.3 USP/mL of trypsin and temperature was lowered to 33° C. During a 8 days virus propagation period, samples were collected daily and stored at −80° C. Left panel: cell density (×10$^6$ cells/mL), right panel: total cell number (yellow rhombus, ×10$^7$ cells) and viability (red circles, %).

FIG. 18B—Hemagglutinin analysis of EB14-derived A/H1N1/NewCaledonia/20/99 influenza virus Samples collected over a 7 days post-infection period were analyzed for detection and quantification of produced HA with a specific polyclonal anti-HA sheep serum. Left panel: western blot analysis of 4 μL of viral supernatant where antigens-captured antibodies were immunostained with an anti-HA sheep antibody together with an anti-sheep-IgG conjugated to peroxydase. HA accumulation is compared with increasing amounts of egg-derived standards reagents. HA0: uncleaved HA subunit, HA1&HA2: cleaved HA subunits. Right panel: SRID quantification of 10 μL of viral supernatant Calculation of HA content is related to a dose-response curve of the same standard reagents.

EXAMPLES

Example 1

Process of Derivation of EBx® Cell Lines

The process of establishment of avian embryonic derived stem cell lines EBx® has been previously described in WO03/076601 and WO05/007840. Briefly, this process of establishment of EBx® cell lines comprises the following steps:
- a) isolation, culture and expansion of avian cells, preferably avian embryonic stem cells, in a complete culture medium containing all the factors allowing their growth and in presence of a feeder layer of mouse fibroblasts, preferably inactivated, and supplemented with animal serum;
- b) passage by modifying the culture medium so as to obtain progressive or total withdrawal of said factors, of said serum and of said feeder layer;
- c) establishing adherent or non adherent avian cell lines capable of proliferating in a basal medium in the absence of exogenous growth factors, inactivated feeder layer and a low level of serum or no serum;

In the event, the basal medium of step c) still comprises a low level of serum (i.e. around 2% or less), said process may optionally comprises an additional step d) of changing the basal medium containing no more exogenous growth factor, no more inactivated feeder layer and a low level of serum with a medium of culture selected among:

a basal medium complemented with serum (i) and diluted with a serum-free medium, then culturing during successive passages said avian cells in the basal medium (i) in which the ratio of serum-free medium is progressively increased up to the complete disappearance of said basal medium containing no exogenous growth factor, no inactivated feeder layer and no serum;

a serum-free medium complemented with serum (ii), then culturing during successive passages said avian cells in said medium (ii) in which the ratio of serum is progressively decreased up to the obtaining of a serum-free medium;

a serum-free medium (iii), then culturing said avian cells in medium (iii); then maintaining in serum-free medium said avian cells adapted to the medium change.

The term "factor allowing their growth" as used herein meant growth factor necessary for the survival and the growth of the avian cells in culture. According to the invention, the growth factors comprises trophic factors and cytokines. Trophic factors are mainly SCF, IGF-1 and bFGF. Cytokines are mainly cytokines whose action is through a receptor which is associated with the gp130 protein such as LIF, interleukin 11, interleukin 6, interleukin 6 receptor, CNTF, oncostatin and cardiotrophin.

The avian cells of step a) are cells selected among avian embryonic cells, more preferably among avian embryonic stem cells and avian primary cells. In a preferred embodiment, the cells are totipotent or pluripotent avian embryonic stem cells isolated from a population suspension of dissociated stage X blastodermal cells obtained from an avian embryo, more preferably a chicken embryo (see EYAL-GILADI's classification: EYAL-GILADI and KOCHAN, 1976, <<From cleavage to primitive streak formation: a complementary normal table and a new look at the first stages of the development in the chick>>. "General Morphology" Dev. Biol. 49: 321-337). These avian embryonic stem cells are characterized by a slow doubling time comprises between 48 to 72 hours in culture at 39° C.

The modification of the culture medium of step b) of the process of establishment EBx® cell lines, so as to obtain progressive or total withdrawal of growth factors, serum and/or feeder layer, can be made simultaneously, successively or separately. The sequence of the weaning of the culture medium may be chosen among:
- feeder layer/serum/growth factors;
- feeder layer/growth factors/serum;
- serum/growth factors/feeder layer;
- serum/feeder layer/growth factors;
- growth factors/serum/feeder layer;
- growth factors/feeder layer/serum.

In a preferred embodiment, the sequence of the weaning is growth factors/feeder layer/serum.

This process allows a selection of cell clones which are adapted to these new, increasingly drastic culture conditions until stable lines are obtained which are capable of growing in a serum-depleted medium or in a medium completely free of serum. The established lines EBx® are preferably non adherent stem cells which proliferate in suspension in a medium free of exogenous growth factors and serum without feeder cells.

By "complete culture medium", it is meant a basal medium complemented with growth factors and animal serum. Example of complete culture medium is described in Pain et al. (1996, Development 122:2339-2348), EP 787,180 and U.S. Pat. No. 6,114,168, U.S. Pat. No. 5,340,740, U.S. Pat. No. 6,656,479 and U.S. Pat. No. 5,830,510. According to the invention, "basal medium" meant a medium with a classical media formulation that allows, by itself, at least cells survival, and even better, cell growth. Examples of basal media are SFM media as previously described or media such as BME (basal Eagle Medium), MEM (minimum Eagle Medium), medium 199, DMEM (Dulbecco's modified Eagle Medium), GMEM (Glasgow modified Eagle medium), DMEM-HamF12, Ham-F12 and Ham-F10, Iscove's Modified Dulbecco's medium, MacCoy's 5A medium, RPMI 1640. Basal medium comprises inorganic salts (for examples: $CaCl_2$, KCl, NaCl, $NaHCO_3$, $NaH_2PO_4$, $MgSO_4$, . . . ), aminoacids, vitamins (thiamine, riboflavin, folic acid, D-Ca panthothenate, . . . ) and others components such as glucose, beta-mercaptoethanol, sodium pyruvate.

It is possible to schematically distinguish two families of growth factors: the cytokines and the trophic factors. The cytokines are mainly cytokines whose action is through a receptor which is associated with the gp130 protein. Thus, LIF, interleukin 11, interleukin 6, interleukin 6 receptor, CNTF, oncostatin and cardiotrophin have a similar mode of action with the recruitment at the level of the receptor of a specific chain and the combination of the latter with the gp130 protein in monomeric or sometimes heterodimeric form. The trophic factors are mainly SCF, IGF-1 and bFGF. More preferably, the complete medium comprises basal medium, Insulin Growth factor 1 (IGF-1), Ciliary Neurotrophic factor (CNTF), Interleukine 6 (IL-6), interleukine 6 receptor (IL-6R), Stem cell Factor (SCF), basic Fibroblast Growth Factor (bFGF), optionally interleukine 11 (IL-11) and animal serum. The avian cells, preferably the avian embryonic cells of step a) are cultured during several passages in the complete medium. The medium is complemented by at least one of the growth factors selected in the group of: LIF, IGF-1, CNTF, IL-6, IL-6R, SCF, bFGF, IL-11, oncostatin, cardiotrophin. According to a preferred embodiment, the complete culture medium is basal medium complemented with IGF-1 and CNTF. According to another preferred embodiment, the complete culture medium is basal medium complemented with IGF-1, CNTF, IL-6, IL-6R, SCF, bFGF, optionally IL-11. The concentration of growth factors IGF-1, CNTF, IL-6, IL-6R, SCF, bFGF, optionally IL-11 in the basal medium is comprised between about 0.01 to 10 ng/ml, preferably, 0.1 to 5 ng/ml, and more preferably about 1 ng/ml.

After around passages 3 to 10, the complete medium is depleted in growth factors (step b). Preferably, for each growth factor, the depletion is made directly in one step, from one passage to another. Alternatively, the growth factor depletion is performed gradually, by a progressive decrease of the growth factor concentration in the complete medium. In a more preferred embodiment, the growth factors depletion is performed simultaneously for at least two growth factors. In a preferred embodiment, when the complete culture medium is basal medium complemented with IGF-1 and CNTF. the depletion in growth factors is made in one round of depletion. In another preferred embodiment, when the complete culture medium is basal medium complemented with IGF-1, CNTF, IL-6, IL-6R, SCF, bFGF, optionally IL-11. the depletion in growth factors is made in two rounds of depletion: firstly, SCF, IL6, IL6R, bFGF optionally IL11 are directly removed from the complete medium; the avian cells are then maintained in culture for at least one passage in a complete medium containing IGF1 and CNTF, optionally IL-11, and supplemented with animal serum. Secondly, IGF1 and CNTF, optionally IL-11 are directly removed from the culture medium, which ultimately comprises the basal medium only supplemented with serum. Usually, the medium is totally depleted in growth factors at around passages 20 to 30.

In a preferred embodiment, the deprivation of feeder cells is performed after the deprivation of growth factors. The deprivation of feeder cells is progressive and performed over several passages. The avian cells are now seeded in flask at a lower concentration than in step a), about around $4\times10^4$ cell/cm$^2$ to $5\times10^4$ cell/cm$^2$. The feeder cells are seeded in flask at around $4.2\times10^4$ cell/cm$^2$. Progressively, the concentration of the feeder cells in the flask is decreased. Practically, the same concentration of the feeder cells is used for 2 to 4 passages, then a lower concentration of the feeder cells is used for an additional 2 to 4 passages, and so. The flask is then seeded with around $4.2\times10^4$ feeder Cells/cm$^2$, then around $2.2\times10^4$ feeder cells/cm$^2$, then around $1.8\times10^4$ feeder cells/cm$^2$, then around $1.4\times10^4$ feeder cells/cm$^2$, then around $1.1\times10^4$ feeder cells/cm$^2$, then around $0.9\times10^4$ feeder cells/cm$^2$, then around $0.5\times10^4$ feeder cells/cm$^2$. Then the flask is seeded with $6.5\times10^4$ avian cells/cm$^2$ to $7.5\times10^4$ avian cells/cm$^2$ and without feeder cells. In the hypothesis that avian cells are not in good shape following a decrease of feeder cells concentration in the flask, then the avian cells are cultured for additional passages with the same feeder cells concentration before to pursue the feeder cells deprivation.

In another preferred embodiment, the serum deprivation is performed after the growth factor and the feeder cells deprivation. The basal medium is changed by a medium selected among:

The basal medium (i) complemented with serum and diluted with a novel serum free medium (ii). Then the avian cells are cultured through successive passages in the medium (i) in which the serum free medium proportion is progressively increased up to the complete disappearing of the basal medium complemented in serum (progressive dilution).
A novel serum free medium (ii) complemented with serum. Then the avian cells are cultured through successive passages in the medium (ii) in which the serum proportion is progressively decreased up to the obtaining of a serum-free medium (progressive weaning).
A novel serum free medium (ii) non complemented with serum. Then the avian cells are directly in the serum-free medium (ii) (direct weaning).

In a preferred embodiment, the serum deprivation is performed by progressive weaning.

The feeder cells are animal cells that have been preferably inactivated by irradiation or chemically treated with mitomycin. The feeder may be genetically modified to express growth factors such as SCF. Preferably, the feeder cells are mouse fibroblasts cell lines such as STO (American Type Culture Collection ATCC N°CRL-1503).

This process leads to the establishment of avian embryonic derived cell lines named EBx® which are maintained in culture in vitro over a considerable period of time. Advantageously, the EBx® cells obtained in step c) are capable of proliferating for at least 50 days, 100 days, 150 days, 300 days or preferably at least 600 days. The 600 days do not constitute a time limit because the EBx® cells obtained are still alive after much longer time periods. For example a Master Cell Bank of EB14 cells has been produced at passage P160 and an EB14 End of Production cell bank has been produced at P184 and EB14 cells are still able to proliferate. Hence, these lines are considered as being able to grow indefinitely in a basic culture medium free of exogenous growth factors, serum and/or inactivated feeder layer. The expression "line" is understood to mean any population of cells capable of proliferating indefinitely in culture in vitro while retaining to a greater or lesser degree the same morphological and phenotypic characteristics. Of course, the method mentioned above makes it possible to obtain cellular clones derived from cells obtained from established lines. These clones are cells which are genetically identical to the cell from which they are derived by division.

The established cell lines and the cells derived thereof (step c or d) are preferably embryonic derived avian stem cells lines, more precisely those cells are pluripotent avian embryonic derived stem cells. The avian embryonic derived stem cells EBx® obtainable by the process of the invention are small, round, individualized cells with a doubling time of around 24 hours or less at 39° C. The cells obtainable by the process of the invention are at least at passage p60, at least p70, at least p80, at least p90, at least p100, at least p110 at least p120, at least p130, at least P150, at least P160, at least P170, at least P180 or later. The avian embryonic derived stem cells according to the invention have at least one of the following characteristics:

a high nucleo-cytoplasmic ratio,
an endogenous alkaline phosphatase activity,
an endogenous telomerase activity,
a reactivity with specific antibodies against SSEA-1 (TEC01), SSEA-3, and EMA-1.
They express the ENS1 gene;
A doubling time shorter than the doubling time of the avian cells of step a) of the process of the invention (48 to 72 h at 39° C.), of about 24 hours or less in the same culture conditions. These EBx® cell lines are capable of proliferating indefinitely in a basal medium, in particular in a medium such as SAFC Excell media, DMEM, GMEM, HamF12 or McCoy supplemented with various additives commonly used by persons skilled in the art. Among the additives, there may be mentioned non-essential amino acids, vitamins and sodium pyruvate, fatty acids, yeast and soy hydrolyzates. However, the cells are able to proliferate in basal medium without glutamine. These cells lines and the cells derived there from have the characteristic to grow either as adherent cells or as suspension cells.

Preferably, the EBx® cells of the invention, preferably EB14 cells, have all the above mentioned characteristics and are useful for the production of biologics such as viral vaccines and recombinant peptides and proteins (i.e. antibodies, . . . ).

Example 2

Characterization of EB14 Cells 2.1—EB14 Cells Karyotype

Karyotyping analysis of EB14 cells has been performed in Pr. Michel Franck Laboratory, Unité de zootechnie, ethnologie et économie rurale, Ecole Nationale Vétérinaire, 1 avenue Bourgelat, 69280 Marcy l'Etoile, France.

EB14 cells were karyotyped at two different passages (Passage 105 and 118) by using standard techniques well-known to the man skilled in the art. As expected, EB14 cells at passage 105 and 118 display a diploid karyotype (FIG. 2):

Passage 105: modal number of chromosomes=78 (average mean: 78.41—standard deviation: 4.951 over 53 studied metaphases)

Passage 118: modal number of chromosomes=79 (average mean: 79.68—standard deviation: 3.733 over 50 studied metaphases).

Chicken genome comprises two types of pairs of chromosomes: macro- and micro-chromosomes. Passage 115 analysis shows that the modal number of macro-chromosomes is 18 with an average mean of 17.82 and a standard-deviation of 0.833 and a modal number of micro-chromosomes of 60 with an average mean of 60.6 and a standard-deviation of 4.7. Passage 118 analysis shows that the modal number of macro-chromosomes is 18 with an average mean of 18.24 and a standard-deviation of 0.797 and a modal number of micro-chromosomes of 60 with an average mean of 61.44 and a standard-deviation of 3.688. There is no significant deviation in chromosomes distribution between the two studied passages. EB14 cell line displays a normal male (ZZ) diploid karyotype at passages 105 and 118 that demonstrates the chromosomal stability of EB14 cells.

2.2—Tumorigenicity Analysis of EB14 Cells in the Immuno-Suppressed New-Born Rat Model Tumorogenicity if EB14 cells at passage 127 has been assessed in the immuno-suppressed new-born rat model (Sanofi-Aventis, France) (WHO technical report N° 878 (1998). Hela cells were used as positive controls. Ten immuno-suppressed new-born rats were injected sub-cutaneously with 10 million EB14 cells and ten additional immuno-suppressed new-born rats were injected sub-cutaneously with 10 million Hela cells. All animals received 0.1 ml of anti-thymocyte rat serum at days 0, +2, +7 and +14. Animals were regularly observed during three weeks to detect nodules at the injection site. After 3 weeks, animals were killed and examined to detect cell proliferation at the injection site and in other organs. No nodules or tumors were observed at the EB14 cells injection site or in distant organs. EB14 are non-tumorigenic in the immuno-suppressed new-born rat model.

2.3—EB14 Cells Express Avian and Human Influenza Virus Receptors

The detection of receptors to avian (Sia 2-3Gal) and human (Sia 2-6Gal) influenza viruses on EB14 cells is performed by fluorescent cell sorter analysis by using digoxygenin labelled lectins (Boehringer):

Sambuca nigra (SNA) agglutinin lectin specifically binds to Sia 2-6Gal;

Maackia amurensis (MM) agglutinin lectin specifically binds to Sia 2-3Gal.

EB14 and MDCK cell lines were washed in 10 mM HEPES, 150 mM NaCl pH7.5 and resuspended in the same buffer at a $5.10^6$ final concentration. Cells were incubated 30 min on ice, then for an additional 15 to 30 minutes in presence of SNA or MM. Lectin treated cells were washed in 10 mM HEPES, 150 mM NaCl pH7.5, prior to incubation on ice during 15 to 30 minutes with FITC-labelled anti-digoxygenin antibody. Then cells are washed in NaCl 0.9% and FACS analyzed.

EB14 cells express cell surface receptors comprising oligosaccharides with Sia 2-6Gal and Siaα2-3Gal residues (FIG. 6).

Example 3

MVA Production in EB14 Cells 3.1—Materials and Methods

Recombinant MVA virus encoding green fluorescent protein gene was used. Titration of infectious MVA-GFP viruses was performed on DF-1 cells. In brief, cells were seeded in 96 flat-bottom well plates at a density of $15.10^3$ cells/well in DMEM medium (Biowhittaker) supplemented with 5% foetal calf serum (FCS) (SAFC) and 2 mM L-glutamin (Biowhittaker). Twenty-four hours later, cells were infected with ten fold serially diluted samples in DMEM and incubated for one week at 37° C., 5% $CO_2$ in a humidified atmosphere. Virus infectivity was measured through microscopic observation of global cytopathic effect (CPE) and UV-exposed infected cells. Then TCID50 titers were calculated according the Reed and Muench method (1938, A simple method of estimating fifty percent endpoints. Am. J. Hyg. 27, 493-97).

3.2—Infection in Tissue Culture Flasks 3.2.1—Materials

| | |
|---|---|
| Vessel: | F175 flask (Starstedt, Ref. 83 1812502) |
| Orbital Agitator: | IKA KS260 or equivalent |
| Sonicator: | IKA U50 (monitored with US50-3 probe) |
| Medium: | Excell 65319 (SAFC-JRH) with 2.5 mM Glutamine (Cambrex Ref. BE17605E); |

3.2.2—Methods

Step 1: EB14 Cells Preparation

Cells should be prepared 2 weeks before starting the infection experiment.

Day 0: EB14 cells are seeded in F175 flask at $0.4 \times 10^6$ cells/mL in 25 ml of Excell 65319 medium with 2.5 mM Glutamine [$1^{st}$ seeding after clumps breaking]. Cells are incubated at 37° C., 7.5% $CO_2$, Humidified atmosphere under agitation (60 rpm)

Day 1: 25 ml of Excell 65319 medium with 2.5 mM Glutamine are added.

Day 2: 50 ml of Excell 65319 medium with 2.5 mM Glutamine are added.

Day 3: Cells are numbered. An aliquot of EB14 cells is seeded in a new F175 flask at $0.4 \times 10^6$ cells/mL in 25 ml of Excell 65319 medium with 2.5 mM Glutamine. This represents the dilution +1.

Day 4: 25 ml of Excell 65319 medium with 2.5 mM Glutamine are added.

Day 5: 50 ml of Excell 65319 medium with 2.5 mM Glutamine are added.

Day 6: Cells are numbered. An aliquot of EB14 cells are seeded in a new F175 flask at $0.4\times10^6$ cells/mL in 25 ml of Excell 65319 medium with 2.5 mM Glutamine. This represents the dilution +2.

Then, the amplification of the cells continues this way, up to a dilution comprises preferably between +3 to +7, more preferably +3 to +5. Then one should proceed with step 2 of cells infection.

To obtain a cell culture containing large clumped EBx® cells (hereinafter named: "large clumps" conditions), when the cells are passaged by dilution to larger vessel(s), the EBx® cells are not centrifuged, and the dumps are not broken by pipetting and stirring. In the opposite, to obtain a cell culture without a substantial proportion of clumped EBx® cells, the dumps are disrupted by pipetting or stirring when passaging the cells (hereinafter named: "no clumps" conditions).

Step 2: Infection of EB14 Cells with MVA-DFP (Green Fluorescent Protein).

Day 1: EB14 cells are seeded in F175 flask at $0.4\times10^6$ cells/mL in 40 mL JRH Excell 65319 medium with 2.5 mM Glutamine. Cells are incubated at 37° C., 7.5% $CO_2$, Humidified atmosphere under agitation (60 rpm).

Days 2 and 3: Cells are numbered.

Day 4: Cells are numbered. When cell density in the flask is about $4\times10^6$ cells/ml, EB14 cells are infected with a MOI of 0.01 $TCID_{50}$/cell with 1 ml viral infection mix per flask. Viral infection mix is prepared just before use by virus dilution in Excell 65319 medium with 2.5 mM Glutamine. Each inoculum is sonicated 30 sec (amplitude 100% and continuous cycle) on ice in 15 ml Falcon™ tube. Inoculum is warmed at room temperature before mixing with the cell culture. Following inoculation, the infected culture medium is incubated 1 h at 37° C. Then, 60 ml of fresh medium Excell 65319 supplemented with 2.5 mM Glutamine, 0.5× Yeastolate and 0.35 ml/L fatty acids is added in the flask. The infected cell culture is further incubated at 37° C. during at least 144 h (nb: the viral production peak is between pi+72 h and pi+120 h).

Cell culture samples (1 mL) are collected every 24 h and keep frozen at −80° C. Prior the sample collection, cell culture is homogenized by gentle pipetting. Virus titration on every collected samples is performed at the end of the experiment using TCID50/mL Reed and Muench's method (1938).

3.3—Infection in Spinner 3.3.1—Materials

| Vessel: | 500 ml & 1 liter spinner bottle (Corning) |
|---|---|
| Orbital Agitator: | IKA KS260 or equivalent |
| Sonicator | IKA U50 (monitored with US50-3 probe) |
| Medium: | Excell 65319 (SAFC-JRH) with 2.5 mM Glutamine (Cambrex Ref. BE17605E); |

3.3.2—Method

Step 1: EB14 Cells Preparation

Cells should be prepared 2 weeks before starting the infection experiment.

Day 0: EB14 cells are seeded in F175 flask at $0.4\times10^6$ cells/mL in 25 ml of Excell 65319 medium with 2.5 mM Glutamine [1st seeding after clumps breaking]. Cells are incubated at 37° C., 7.5% $CO_2$, Humidified atmosphere under agitation (60 rpm)

Day 1: 25 ml of Excell 65319 medium with 2.5 mM Glutamine are added.

Day 2: 50 ml of Excell 65319 medium with 2.5 mM Glutamine are added.

Day 3: Cells are numbered. An aliquot of EB14 cells is seeded in a new F175 flask at $0.4\times10^6$ cells/mL in 25 ml of Excell 65319 medium with 2.5 mM Glutamine. This represents the dilution +1.

Day 4: 25 ml of Excell 65319 medium with 2.5 mM Glutamine are added.

Day 5: 50 ml of Excell 65319 medium with 2.5 mM Glutamine are added.

Day 6: Cells are numbered. An aliquot of EB14 cells are seeded in a new F175 flask at $0.4\times10^6$ cells/mL in 25 ml of Excell 65319 medium with 2.5 mM Glutamine. This represents the dilution +2.

Then, the amplification of the cells continues this way, up to a dilution comprises preferably between +3 to +7, more preferably +3 to +5. Then one should proceed with step 2 of cells infection.

To obtain a cell culture containing large clumped EBx®® cells (hereinafter named: "large clumps"), when the cells are passaged by dilution to larger vessel(s), the EBx® cells are not centrifuged, and the clumps are not broken by pipetting and stirring. In the opposite, to obtain a cell culture without a substantial proportion of clumped EBx® cells, the clumps are disrupted by pipetting or stirring when passaging the cells (hereinafter named: "no clumps").

Step 2: EB14 Cells Infection with MVA-GFP

Day 1: EB14 cells are seeded in 500 ml (or 1,000 ml) spinner bottle at $0.4\times10^6$ cells/mL in 150 mL (or 300 ml) JRH Excell 65319 medium with 2.5 mM Glutamine. Cells are incubated at 37° C., 7.5% $CO_2$, Humidified atmosphere under agitation (100 rpm).

Days 2 and 3: Cells are numbered.

Day 4: Cells are numbered. When cell density in the spinner is about $4\times10^6$ cells/ml, EB14 cells are infected with a MOI of 0.01 $TCID_{50}$/cell with 1 ml viral infection mix per spinner bottle. Viral infection mix is prepared just before use by virus dilution in Excell 65319 medium with 2.5 mM Glutamine. Each inoculum is sonicated 30 sec (amplitude 100% and continuous cycle) on ice in 15 ml Falcon™ tube. Inoculum is warmed at room temperature before mixing with the cell culture. Following inoculation, the infected culture medium is incubated 1 h at 37° C. Then, 60 ml of fresh medium Excell 65319 supplemented with 2.5 mM Glutamine, 0.5×Yeastolate and 0.35 ml/L fatty acids is added in the 500 ml (or 1,000 ml) spinner bottle. The infected cell culture is further incubated at 37° C. during at least 144 h (nb: the viral production peak is between pi+72 h and pi+120 h).

Cell culture samples (1 mL) are collected every 24 h and keep frozen at −80° C. Prior the sample collection, cell culture is homogenized by gentle pipetting. Virus titration on every collected samples is performed at the end of the experiment using TCID50/mL Reed and Muench's method (1938)*.

*Reed L & Muench H (1938) A simple method of estimating fifty percent endpoints. *Am. J. Hyg.* 27, 493-97.

3.4—Infection in 3 L-Stirred Tank Bioreactor 3.4.1—Method

Cell Thawing

Cell cryovials are stocked in liquid nitrogen at −196° C.; each cryovial contains $20.10^6$ cells. The cryovial are directly thawed in a 37° C. prewarmed water bath to rapidly thaw the frozen vial. The cell suspension is pipette into a 50 mL PP sterile tube with 30 mL pre-warmed culture medium. The cell suspension is centrifuged 5 min at 300±20 g, at room temperature, the supernatant is discarded and the pellet is resuspended in 15 ml of fresh culture medium and gently homogenise. The cell suspension are plated into a T75 $cm^2$ flask and is incubated at 37° C. under a 7.5% $CO_2$ atmosphere on an orbital shaker at 50 rpm. After 24 hours and 48 hours of culture, 15 ml of pre-warmed culture medium is added to the cell culture. After 72 hours of culture, a sample is collected (after bulk homogenisation) and a numeration is performed: $\geq 40.10^6$ cells are expected. Then the first amplification is performed.

First Cell Amplification: Centrifugation, Dissociation and Dilution

The suspension cells are collected from the flask(s) in 50 mL PP sterile tube(s). After 5 min of centrifugation at 300±20 g, at room temperature, the supernatant is discarded and 10 mL of prewarmed fresh culture medium is added on the pellet(s). The cell dumps are gently dissociated with a 10 mL pipette and the cell suspensions are pooled in one 50 mL PP sterile tube if necessary. The culture volume is completed up to 20 mL with fresh prewarmed culture medium if necessary. A numeration is performed using trypan blue to determine cell density and cell viability (cell viability is typically around 80%). In 1 T175 cm$^2$ flask, $0.4.10^6$ cells.mL$^{-1}$ are seeded in 40 ml of prewarmed culture medium. The cell culture is incubated at 37° C. under an 7.5% $CO_2$ atmosphere on an orbital shaker at 50 rpm. At day 2, 60 ml of pre-warmed culture medium is added to the cell culture. At day 3, cell dilution are performed.

Dilution +1 to +5 (No Centrifugation, No Dissociation, Only Dilution).

A sample is taken from the T175 flask (after gently mixing) to perform a numeration using tryptan blue to determine cell density. A sample is taken from the T175 flask (after gently mixing) in order to seed $0.4.10^6$ cells.mL$^{-1}$ in 1 T175 cm$^2$ flask in a total volume of 25 ml of pre-warmed culture medium. This represents dilution +1.

At day 1, 50 ml of pre-warmed culture medium is added. At day 2, Dilution +2 is performed using the same way that for dilution +1 (see above). The cells amplification is performed this way, up to Dilution +3 to +5. The Inoculum for the 3 L bioreactor can be prepared from Dilution +3 until Dilution +5. Two T175 flasks are prepared as an inoculum.

Cells seeding in 3 L Stirred-thank bioreactor

Seeding—Day 0

The inoculum is prepared ($320.10^6$ cells are needed to inoculate the 3 L-bioreactor). The 2 T175 flasks are pooled. A sample is taken after gently mixing (cells clumps should not be broken) to perform a numeration using trypan blue to determine cell density. A 150 mL cell mix is prepared in order to obtain a cell concentration of $0.40.10^6$ cells.mL$^{-1}$ into the 800 ml final culture volume in the bioreactor.

Prior to seed cells, the pH is set in the vessel to 7.2 (because pH will be decrease by $CO_2$ surface injection). The $pO_2$ is set to 50% $O_2$ saturation (the mass flow controller is adjusted to 100% which correspond to a maximum sparger flow rate to 50 mL.min$^{-1}$). At the beginning of the process, the pH is maintained by $CO_2$ surface injection, later, it is controlled by addition of 7.5% $NaHCO_3$. The surface aeration is started with air at a flow rate of 0.3 mL.min$^{-1}$.

Culture Follow-Up/Feed Addition (Day 1, Day 2)

Cell numeration is performed on a routine basis. The metabolites such as glutamate, glutamin, lactate and glucose are analyzed all along the culture with the BioProfile Basic software. Concentration of the metabolites is adjusted if necessary. For example, Glutamin concentration is adjusted to 2 mM.

Infection with MVA-GFP(Day 3)

After 3 days of culture, the cell density should be higher than $3.10^6$ cells.mL$^{-1}$. If the target cell density is reached (3 to $5.10^6$ cells.mL$^{-1}$), the virus infection is performed at a MOI of 10.2 TCID$_{50}$/cell. The virus strain is thawed on ice. The infection mix is prepared in a 50 mL PP sterile tube with 10 mL of production medium. The mix is sonicated during 30 sec (amplitude 100% and continuous cycle) on ice. The infection mix is inoculated into the bioreactor. After 1 hour of viral adsorption, the final production medium is added to the vessel. The 1.5 L Excell 65319 production medium in 1.5 L is supplemented with Yeastolate and Fatty Acids to a final concentration of respectively 0.5× and 0.35 ml/L (final volume: 2.3 L).

Production following/Feed addition (Day 4, Day 5, Day 6, Day 7, Day 8, Day 9, Day 10)

The MVA viral production peak is reached between 72 h and 120 h post infection. Every day a sample of approximatively 15 ml is collected from the bioreactor to perform cell numeration, cell morphology analysis and to observe CPE. The metabolites such as glutamate, glutamine, lactate and glucose are analyzed all along the culture with the BioProfile Basic software. Concentration of the metabolites is adjusted if necessary. For example, glutamine concentration is adjusted to 2 mM if necessary. The glucose concentration is adjusted to 2 g.L$^{-1}$ if necessary.

Analyses

Virus titration is carried-out at the end of the experiment using all collected samples.

3.5—Results 3.5.1—Cell growth kinetics of EB14 cells in a 3 L fedbatch bioreactor EB14 cells are routinely cultured in stirred-tank bioreactor. EB14-derived biomass is allowed to accumulate at 37° C. in a cell growth medium until a cell density of $5-6.10^6$ cells/mL was reached. Then the mixture is around 3 fold diluted and cell growth kinetic is followed-up over a 10 days period. In such conditions, cell density of 12 to 16 million cells/ml is routinely reached around day 5 to 8 (FIG. 7A). EB14 cells splitting ratio may be increased. FIG. 7B shows a growth kinetic of EB14 cells diluted 10 fold.

3.5.2—EB-14 Cells Flexibility: Plaque Purification of MVA-GFP Virus on Adherent Cells EB14 cells grow in suspension culture. However, EB14 cells have also the ability to grow in adherence in flask and plates. This feature allow the inventors to perform plaque purification of MVA-GFP on adherent EB14 cells. To do so, ten fold serial dilutions of MVA-GFP virus were inoculated on adherent EB-14 cells seeded in 6 well plates 24 h before at a density of $7.10^4$ cells/cm$^2$. Following virus adsorption, cells were over layered with a mix of 1.2% LMP agarose/2.5% FCS DMEM and incubated at 37° C. for several days. Wells were finally stained with neutral red. Plaque forming unit titration can then be calculated with dilutions providing isolated plaques.

3.5.3—Influence of Production Medium and Clumps Size for MVA-GFP Virus Propagation in Infected EB14 Cells EB14 were allowed to form small or large dumps in T175 stirred tank flasks during cell proliferation in a cell growth medium (Excell 65319). Clumps were then infected with $10^{-2}$ TCID$_{50}$/cell of MVA-GFP virus and the mixture was diluted in several production media (Optipro, Excell 319, Excell 421, Excell 625, Excell 626, Excell 627, Excell 628, Excell 629, G9916). The presence of large clumps of EB14 cells improves virus infection and propagation (FIG. 8), leading to higher MVA virus titers (FIG. 9). The addition of supplements such as yeastolate (supplement 1) and Fatty acids (supplement 2), in the virus production medium further improves MVA virus titers. As shown in FIG. 10, when yeastolate 1× (supplement 1) is added alone into the medium, MVA-GFP viral yield is increased and a synergistic effect is even obtained when adding yeastolate (supplement 1) and Fatty acids (supplement 2) in the cell growth medium. Indeed, fatty acid 1× alone does not increase viral titers.

3.5.4—MVA Virus Production in 3 L-Bioreactor

EB14-derived biomass was allowed to accumulate during cell proliferation phase in Excell 65319 growth medium. Cells were then infected with $10^{-2}$ TCID$_{50}$/cell of MVA-GFP virus and the mixture was diluted in Excell 65319 production medium. Following addition of Excell 65319, cell density dropped down (day 3), and at day 5, the cell density of infected cells increased and reached 4 million cell/ml. The fact that no centrifugation is performed during cell amplification allows to get large clumps size in culture 2 to 4 days post-infection (FIG. 11). In such conditions, the MVA-GFP productivity is high. Since at day 6 post-infection, the MVA-GFP titer is around $10^{8.32}$ TCID50/ml (Cell concentration of 1.49×10$^6$ cells/ml) which correspond to TCID50/cell=414 (Amplification factor 41,000) (FIG. 12). It appears that when the EB14 cells are amplified without disrupting the dumps (by dilution for example), a higher viral titer is obtained in 3 L-bioreactor compared to the one obtained in absence of large dumps (Amplification factor around 1900 and TCID50/cell=19) into the cell culture.

3.5.5—Normal Ultrastructure of MVA Infected EB14 Cells

EB14 cells infected with MVA virus were analyzed by electron microscopy (Drs. Daniele Spehner & Robert Drillien, IGBMC, Strasbourg France). The maturation of MVA virus produced in EB14 cells is normal and similar to the one observed in primary chicken embryo fibroblasts.

Example 4

Production of Influenza Virus In EB14 Cells

4.1—Materials & Methods
4.1.1—Influenza Virus Infectivity Assay (TCID50)

Titration of infectious influenza viruses was performed on MDCK cells. In brief, cells were seeded in 96 flat-bottom well plates at a density of 3.10$^3$ cells/well in UltraMDCK medium supplemented with 2.5 mM L-glutamin. Twenty-four hours later, cells were infected with ten fold serially diluted samples in UltraMDCK containing 6 µg.mL$^{-1}$ trypsin-EDTA and incubated for one week at 33° C., 5% CO$_2$ in a humidified atmosphere. Virus replication was then tested in an HA assay using chicken red blood cells and TCID50 titers were calculated according the Reed and Muench method (1938)*.

*Reed L, Muench H, 1938. A simple method of estimating fifty percent endpoints. *Am. J. Hyg.* 27, 493-97.

4.1.2—Single Radial Immunodiffusion Assay (SRID)

The concentration of haemagglutinin in samples derived from influenza virus infected-EB14 cells, was determined as described by Wood and colleagues*. Briefly, glass plates were coated with an agarose gel containing anti-Influenza serum (recommended concentration provided by NIBSC). After the gel has set, 10 µL of appropriate dilutions of the reference and the samples were loaded in 3 mm Ø punched wells. Following a 18-24 h incubation in a moist chamber at room temperature, plates were soaked in 0.9% NaCl and washed in distilled water. The gel was then pressed and dried. The plates were stained on Coomassie Brilliant Blue solution for 15 min and destained twice in a mixture of methanol and acetic acid until clearly defined stained zones became visible. After drying the plates, the diameter of the stained zones surrounding antigen wells were measured in two directions at right angles. Dose-response curves of antigen dilutions against the surface were constructed and the results were calculated according to standard slope-ratio assay methods.

*Wood J M. Et al. "An improved single-radial-immunodiffusion technique for the assay of influenza haemagglutinin antigen: application for potency determinations of inactivated whole virus and subunit vaccines". J Biol Stand. 1977; 5(3):23747).

4.1.3—Western Blot Analysis of Influenza Hemagglutinin Protein

SDS-PAGE was performed as described by Laemmli UK (1970, Cleavage of structural proteins during the assembly of the head of bacteriophage T4. Nature 259:680-685) in 10% polyacrylamide gel. Denatured proteins (1% SDS, 70 mM β-mercaptoethanol) were transferred to polyvinylidene difluoride membrane (hybond P, Amersham) by a semidry blotting procedure (Kyhse-Andersen J (1984) Electroblotting of multiple gels: a simple apparatus without buffer tank for rapid transfer of proteins from polyacrylamide to nitrocellulose. J Biochem Biophys Methods 10:203-209). Blots were blocked for 1 h at room temperature with a mixture composed of 5% fat dry milkpowder in TBST supplemented with 1% FCS (SAFC). Then, the blots were incubated overnight in blocking solution supplemented with specific polyclonal anti-HA sheep serum (1:500 (NIBSC). The blots were washed 6 times with TBST and incubated for 1 h at room temperature with a hrp-conjugated rabbit anti-sheep IgG polyclonal antibody (1:5000 (Rockland) in blocking solution. After 6 washes with TBST, the protein-conjugate complex was finally revealed using chemiluminescence (ECL kit, Amersham) and films (Hyperfilm, Amersham).

4.2—Influenza virus Infection of EB14 cells In 3 L-Bioreactor

4.2.1—Materials and Equipment

Cell Thawing Material
  T75 cm$^2$ flasks (Sarstedt, Cat#831813502)
  Culture medium (serum free medium)
  L-Glutamin 200 mM (Biowhittaker, Cat# BE17-605E)
  Orbital agitator IKA KS260 (Fisher Bioblock, Cat# F35044)

Cell Amplification Material
  T175 cm$^2$ flasks (Sarstedt, Cat#831812502)
  Culture medium (serum free medium): Excell 65319 (JRH, Cat#65319-1000M1687) added with 2.5 mM glutamine
  L-Glutamin 200 mM (Biowhittaker, Cat# BE17605E)
  Yeastolate UF Solution 50× (JRH, Cat#58902-100M)
  D (+) Glucose (45%) (Sigma, Cat# G8769)

Production Material
  Production medium (serum free medium): Excell 65629 (JRH, Cat#65629) supplemented with 2.5 mM gin
  Yeastolate UF Solution 50× (JRH, Cat#58902-100M)
  L-Glutamin 200 mM (Biowhittaker, Cat# BE17605E)
  D (+) Glucose (45%) (Sigma, Cat# G8769)
  Trypsin (Trypzean 1×, Sigma, Cat# T3449)
  7.5% bicarbonate sodium solution (Sigma, Cat#205-6338)
  Influenza virus strain (frozen at 80° C.)

4.2.2—Method

Cell Thawing

Cell cryovials are stocked in liquid nitrogen at −196° C.; each cryovial contains 20.10$^6$ cells). The cryovial is directly thawed into a +37° C. prewarmed water bath. The cell suspension is put into a 50 mL PP sterile tube with 30 mL prewarmed culture medium. After centrifugation (5 min at 300±20 g, at room temperature), 15 mL of fresh culture medium is added on the pellet and gently homogenize. The sample is numbered using trypan blue. Numeration has to be ≧20.10$^6$ cells and viability has to be >70% to guarantee a good culture. The cell suspension is plated into a T75 cm$^2$ flask and incubate at +37° C. under an 7.5% CO$_2$ atmosphere on an orbital shaker at 50 rpm. After 24 hours and 48 Hours of culture, 15 mL of prewarmed culture medium is added to the culture. After 72 hours of culture, a sample is collected (after bulk homogenisation) and numbered: 20 to 30.10⁶ cells are expected. Then perform the first amplification is performed.
First Cell Amplification: Centrifugation, Dissociation and Dilution The suspension cell is collected from the flask(s) in 50 mL PP sterile tube(s) and centrifuge 5 min at 300±20 g, at room temperature. 10 mL of prewarmed fresh culture medium is added on the pellet(s). The cell dumps are gently dissociate and cell suspensions is pooled; the volume is completed to 40 mL with fresh pre-warmed culture medium. In 1 T175 cm² flask, $0.25.10^6$ cells.mL$^{-1}$ is plated in 40 ml of pre-warmed medium and incubated at +37° C. under an 7.5% $CO_2$ atmosphere on an orbital shaker at 50 rpm. At day 2, 60 ml of prewarmed culture medium are added. At day 3, a second round of amplification is performed.

Cells Seeding in 3 L Stirred-Thank Bioreactor
Seeding—Day 0

The inoculum is prepared ($320.10^6$ cells are needed to inoculate the 3 L-bioreactor). The 2 T175 flasks are pooled. A sample is taken after gently mixing (cells clumps should not be broken) to perform a numeration using trypan blue to determine cell density. A 150 mL cell mix is prepared in order to obtain a cell concentration of $0.40.10^6$ cells.mL$^{-1}$ into the 800 ml final culture volume in the bioreactor.

Prior to seed cells, the pH is set in the vessel to 7.2 (because pH will be decrease by $CO_2$ surface injection). The $PO_2$ is set to 50% $O_2$ saturation (the mass flow controller is adjusted to 100% which correspond to a maximum sparger flow rate to 50 mL.min$^{-1}$). At the beginning of the process, the pH is maintained by $CO_2$ surface injection, later, it is controlled by addition of 7.5% $NaHCO_3$. The surface aeration is started with air at a flow rate of 0.3 mL.min$^{-1}$.

Culture Follow-Up/Feed Addition (Day 1, Day 2)

Cell numeration is performed on a routine basis. The metabolites such as glutamate, glutamin, lactate and glucose are analyzed all along the culture with the BioProfile Basic software. Concentration of the metabolites is adjusted if necessary. For example, glutamin concentration is adjusted to 2 mM.

Infection—Day 3

After 3 days of culture, cell density have to be higher than $45.10^6$ cells.mL$^{-1}$. If the target cell density is reached, the virus infection is performed at a MOI of $10^{-4}$. The vessel temperature is set to 33° C. The virus strain is thawed on ice. The infection mix is prepared in 10 mL of production medium. After inoculation of the infection mix into the bioreactor, viral adsorption is performed during 1 hour. The final production medium is prepared: in 1.5 L of production medium, trypsin is added in order to obtain a final concentration in the vessel of 0.3 U.mL$^{-1}$ (2.3 L on the whole) and 0.5× Yeastolate is added. The pre-warmed final production medium is then added.

Production Following/Feed Addition (Day 4, Day 5, Day 6, Day 7, Day 8, Day 9, Day 10)

Every day a sample of approximatively 15 ml is collected from the bioreactor to perform cell numeration, cell morphology analysis and to observe CPE. The metabolites such as glutamate, glutamine, lactate and glucose are analyzed all along the culture with the BioProfile Basic software. Concentration of the metabolites is adjusted if necessary. For example, glutamine concentration is adjusted to 2 mM if necessary. The glucose concentration is adjusted to 2 g.L$^{-1}$ if necessary.

Analyses

Virus titration, haemmaglutinin assays (HAU) and HA antigen quantificatons (western blot, SRID) are carry out at the end of the experiment using all collected samples.

4.3—Results

The inventors demonstrate that EB14 cells are a reliable and efficient cell substrate for the replication of various strains A and B of influenza virus. Influenza virus production can be performed in various vessels, such as flasks and spinner (data not shown) and bioreactors. Reproducible and efficient fedbatch process of production of influenza virus in 3 L and 30 L stirred tank bioreactors were obtained by the inventors. Productivities above 25 mg/l of haemagglutinin are routinely obtained in flasks and Productivities above 35 mg/A of haemagglutinin are routinely obtained in flasks with strains A and B of influenza virus.

The invention claimed is:

1. A process of infecting avian embryonic derived stem cells with a poxvirus and replicating said poxvirus in said avian embryonic derived stem cells, wherein said avian embryonic derived stem cells are obtained by a method comprising the following steps:
    A) culturing avian embryonic stem cells in a complete culture medium complemented in serum containing: i) exogenous growth factors comprising the trophic factors stem cell factor ("SCF"), Insulin Growth Factor ("IGF-1"), and basic Fibroblast Growth Factor ("bFGF"), and cytokines whose action is through a receptor which is associated with the gp130 protein, said cytokines being selected from the group consisting of leukemia inhibitory factor ("LIF"), interleukin 11 ("IL-11"), interleukin 6 ("IL-6"), interleukin 6 receptor ("IL-6R"), ciliary neurotrophic factor ("CNTF"), oncostatin and cardiotrophin; and ii) an inactivated feeder layer;
    B) passaging by modifying the culture medium so as to obtain the withdrawal of said exogenous growth factors, of the serum and/or of the feeder layer; and
    C) establishing an adherent or non-adherent cell culture capable of proliferating in a basal medium in the absence of exogenous growth factors, serum and/or inactivated feeder layer;

wherein said process of infecting and replicating a poxvirus in said avian embryonic derived stem cells comprises the steps of:
    a) proliferating said avian embryonic derived stem cells in a cultivation vessel, in suspension as clumped cells, in a first serum-free medium, allowing said cells to aggregate to each other to form cell clumps,
    wherein the transfer of the cell culture from the culture vessel to another is performed by dilution without disrupting the cell clumps;
    b) infecting said clumped cells with the poxvirus when the cell density is of at least 1.5 million cells/ml;
    c) shortly before infection, simultaneously to infection, or shortly after infection adding to the cell culture a second serum-free medium;
    d) further culturing said infected cells in order to allow virus replication and propagation; and
    e) harvesting said virus;
wherein said cell clumps are maintained during steps, a, b, c, and d.

2. The process of claim 1, wherein the cultivation vessel is a continuous stirred tank bioreactor.

3. The process of claim 1, wherein the first serum-free medium and the second serum-free medium are the same medium.

4. The process of claim 1, wherein the first serum-free medium and/or the second serum-free medium is/are supplemented with at least one ingredient selected from the group consisting of amino-acids, lipids, fatty acids, cholesterol, carbohydrates, protein hydrolyzates of non-animal origin, and mixtures thereof.

5. The process of claim 1, comprising the additional step of feeding the cells with at least one ingredient selected from the group consisting of amino-acids, fatty acids, carbohydrates, protein hydrolyzates of non-animal origin, and mixtures thereof.

6. The process of claim 4, wherein the serum-free medium is/are supplemented with amino-acids selected from the group consisting of asparagine, glutamine, and mixtures thereof.

7. The process of claim 6, wherein the feeding of glutamine is performed during step a) to d) to maintain the glutamine concentration in the medium between 0.5 mM to 5 mM.

8. The process of claim 4, wherein the serum-free medium is/are supplemented with carbohydrates selected from the group consisting of D-glucose and D-galactose or a mixture thereof.

9. The process of claim 8, wherein the feeding of D-glucose is performed during step b) to d) to maintain the D-glucose concentration in the medium around 0.5 g/l to 25 g/l of D-glucose.

10. The process of claim 4, wherein the serum-free medium is/are supplemented with fatty acids selected from the group consisting of palmitic acid, palmitoleic acid, stearic acid, oleic acid, linoleic acid, linolenic acid or a mixture thereof.

11. The process of claim 4, wherein the serum-free medium is/are supplemented with protein hydrolyzates of non-animal origin selected from the group consisting of bacteria tryptone, yeast tryptone, plant hydrolyzates, and a mixture thereof.

12. The process according to claim 1, wherein step c) is performed after infection step b).

13. The process according to claim 1, wherein infection step b) is carried out at an m.o.i (multiplicity of infection) of about 10 to $10^{-6}$.

14. The process according to claim 1, wherein the poxvirus is a naturally occurring poxvirus or a recombinant poxvirus selected from the group consisting of fowlpox virus, canarypox virus, juncopox virus, mynahpox virus, pigeonpox virus, psittacinepox virus, quailpox virus, sparrowpox virus, starlingpox virus, and turkeypox virus.

15. The process according to claim 1, wherein the culturing of step a) is carried out by batch culture, repeated batch culture, fed-batch culture or perfusion culture.

16. The process according to claim 1, wherein the infection in step b) is performed when the cell density is of at least 4 million cells/ml in batch or fed-batch process.

17. The process according to claim 1, wherein the infection in step b) is performed when the cell density is of at least 8 million cells/ml in perfusion process.

18. The process according to claim 1, wherein the pH of the serum-free culture medium in steps a), b), c) and d) is in a range from 6.5 to 7.8.

19. The process according to claim 1, wherein step d) lasts for 2 to 10 days before the harvest.

20. The process according to claim 1, wherein the cell culture is performed at a temperature from 30° C. to 39° C.

21. The process according to claim 1, wherein said avian embryonic derived stem cells in step A) are chicken or duck embryonic stem cells.

22. The process according to claim 1, wherein the poxvirus is a vaccinia virus selected from the group consisting of Lister-Elstree vaccinia virus strain, Modified Vaccinia Ankara (MVA) virus, NYVAC, LC16 m8, CVI78, and other recombinant or non-recombinant vaccinia virus.

23. The process according to claim 1, wherein the poxvirus a Modified Vaccinia Ankara (MVA) virus.

24. The process according to claim 1, wherein the first serum-free medium and the second serum-free medium are different.

25. The process according to claim 1, wherein in step A) said complete culture medium contains IGF-1, CNTF, IL-6, IL-6R, SCF, and bFGF.

26. The process according to claim 25, wherein in step A) said complete culture medium further contains IL-11.

* * * * *